(12) United States Patent
Finnie et al.

(10) Patent No.: US 8,815,291 B2
(45) Date of Patent: Aug. 26, 2014

(54) PARTICLES COMPRISING A RELEASABLE DOPANT THEREIN

(75) Inventors: Kim Suzanne Finnie, New South Wales (AU); Christophe Jean Alexandre Barbe, New South Wales (AU); Linggen Kong, New South Wales (AU)

(73) Assignee: Australian Nuclear Science & Technology Organisation (AU)

(*) Notice: Subject to any disclaimer, the term of this patent is extended or adjusted under 35 U.S.C. 154(b) by 1025 days.

(21) Appl. No.: 11/917,662

(22) PCT Filed: Jun. 19, 2006

(86) PCT No.: PCT/AU2006/000853
§ 371 (c)(1),
(2), (4) Date: Apr. 28, 2008

(87) PCT Pub. No.: WO2006/133519
PCT Pub. Date: Dec. 21, 2006

(65) Prior Publication Data
US 2008/0199523 A1 Aug. 21, 2008

(30) Foreign Application Priority Data
Jun. 17, 2005 (AU) .................................. 2005903192

(51) Int. Cl.
*A61K 9/14* (2006.01)

(52) U.S. Cl.
USPC ........................... 424/484; 428/402; 427/213

(58) Field of Classification Search
CPC ........................... A61K 9/1641; A61K 9/5026
USPC ........................... 424/484; 427/213; 428/402
See application file for complete search history.

(56) References Cited

U.S. PATENT DOCUMENTS

| | | | |
|---|---|---|---|
| 4,224,179 A | 9/1980 | Schneider | |
| 5,185,155 A | 2/1993 | Behan et al. | |
| 5,858,928 A | 1/1999 | Aubert et al. | |
| 6,239,211 B1 | 5/2001 | Keeping et al. | |
| 6,303,149 B1 * | 10/2001 | Magdassi et al. | ............ 424/489 |
| 6,586,479 B2 | 7/2003 | Miller et al. | |
| 6,627,603 B1 | 9/2003 | Bibette et al. | |
| 6,924,116 B2 | 8/2005 | Tan et al. | |
| 2003/0059472 A1 | 3/2003 | Brynjelsen et al. | |
| 2004/0048766 A1 | 3/2004 | Raths et al. | |
| 2004/0082237 A1 | 4/2004 | Farmer et al. | |
| 2004/0180096 A1 | 9/2004 | Prasad et al. | |

FOREIGN PATENT DOCUMENTS

| | | | |
|---|---|---|---|
| JP | 11-221459 A | 8/1999 | |
| JP | 2001-354820 | 12/2001 | |
| JP | 2003533363 | 11/2003 | |
| WO | WO 99/07463 | 2/1999 | |
| WO | WO 00/21504 | 4/2000 | |
| WO | WO 01/01960 A1 | 1/2001 | |
| WO | WO 01/62232 A1 * | 8/2001 | ............... A61K 9/22 |
| WO | WO 01/88540 A1 | 11/2001 | |
| WO | WO 02/20148 | 3/2002 | |
| WO | WO 03/013481 A1 | 2/2003 | |
| WO | WO 03/066209 A1 | 8/2003 | |
| WO | WO 2004/005355 A1 | 1/2004 | |
| WO | WO 2004/043441 A1 | 5/2004 | |
| WO | WO 2006/050579 A1 | 5/2006 | |

OTHER PUBLICATIONS

OCM, ChemicalBook, 2010.*
Ottenbrite et al "Self Catalyzed Synthesis of Organo-Silica Nanoparticles," J. Am. Chem. Soc. 83 (12) 3214-15 (2000).*
Indrajit Roy et al., "Ceramic-Based Nanoparticles Entrapping Water-Insoluble Photosensitization Anticancer Drugs: A Novel Drug-Carrier System for Photodynamic Therapy", J. Am. Chem. Soc. 2003, 125, 7860-7865.
Indrajit Roy et al., "Optical tracking of organically modified silica nanoparticles as DNA carriers: A nonviral, nanomedicine approach for gene delivery", PNAS, Jan. 11, 2005, vo. 102, No. 2, pp. 279-284.
Raphael M. Ottenbrite et al., "Self-Catalyzed Synthesis of Organo-Silica Nanoparticles", J. Am. Ceram. Soc. 83 [12] 3214-3215, 2000.
J.S. Wall et al., "Monolayer Grafting of Organo-Silica Nanoparticles on Poly(ethylene naphthalate) Films", Langmuir 2001, 17, 6027-6029.
Sharaboni Das et al., "Inorganic-Organic Hybrid Nanopartides from n-Octyl Triethoxy Silane", Journal of Colloid and Interface Science 252, 82-88, (2002).
S. Shibata et al., "Formation of Dye-Doped Silica Particles", Proc. Int. Workshop on Silica Glasses Jpn. J. Appl. Phys. vol. 37 (1998) Suppl. 37-1, pp. 41-44.
English Translation Notice of Reasons for Rejection Japanese Patent Application No. 2008-516080 dated Dec. 7, 2011.
Paula C.A. Jeronimo et al., "Development of a sol-gel optical sensor for analysis of zinc in pharmaceuticals", Sensors and Actuators B 103, (2004) 169-177.
Xiaoxiao He et al., "A Novel Fluorescent Label Based on Organic Dye-Doped Silica Nanoparticles for HepG Liver Cancer Cell Recognition", J. Nanosci. Nanotech. 2004, vol. 4, No. 6, pp. 585-589.
Toshiyuki Yokoi et al., "Synthesis of Anionic-Surfactant-Templated Mesoporous Silica Using Organoalkoxysilane-Containing Amino Groups", Chem. Mater. 2003, 15, 4536-4538.
Supplementary European Search Report EP 06 74 1256 Dated May 25, 2011.

\* cited by examiner

*Primary Examiner* — Suzanne Ziska
(74) *Attorney, Agent, or Firm* — Baker & Hostetler LLP

(57) ABSTRACT

A process for making particles comprising a hydrophobic dopant for subsequent release therefrom is disclosed. The process comprises providing an emulsion comprising a hydrophilic phase and a hydrophobic phase dispersed in the hydrophilic phase, and reacting the precursor material to form the particles comprising the dopant therein. The hydrophobic phase comprises a precursor material and the dopant.

13 Claims, 18 Drawing Sheets a    b

PARTICLES COMPRISING A RELEASABLE DOPANT THEREIN

TECHNICAL FIELD

The present invention relates to particles having dopants such as hydrophobic materials therein for release, and to processes for making such particles. The particles may be solid or gel particles.

BACKGROUND OF THE INVENTION

For the last decade, the encapsulation and controlled release of hydrophobic species has attracted considerable interest due to the increasing number of industrial applications using hydrophobic/lipophilic active molecules. For example, in the pharmaceutical and agricultural industries, many drugs or biocides possess hydrophobic properties. Nevertheless, the means to encapsulate and controllably release these active molecules remain a challenge for these industries. On the other hand, in food, cosmetics and personal care, encapsulation and controlled release of volatile organic compounds such as flavours and perfumes, or reactive compounds such as bleaches, is becoming a dominant trend for product improvement.

Compared with traditional organic materials, inorganic matrices and more specifically ceramics have many intrinsic advantages. In particular, they are biologically inert, intrinsically hydrophilic, and represent higher mechanical strength and thermal stability. This has prompted some research in this emerging area. However, it is important to note that few of the novel inorganic delivery systems have achieved precise controlled release of the encapsulated molecules.

Such a controlled release technology has been described in "Controlled release ceramic particles, compositions thereof, processes of preparation and methods of use", Barbe, C. J. A. and Bartlett, J., WO 01/62232 (2001). A disadvantage with the technology described by Barbe, et al. is that it only encompasses the incorporation of hydrophilic species. Hydrophobic molecules are excluded because silica formation occurs inside the hydrophilic 'droplets' of a water-in-oil emulsion (see FIG. 1). Hydrophobic molecules added to such a reaction mixture will be located in the external oil phase (nonpolar solvent) and thus will not be incorporated inside the silica particle as they are formed.

Modifications to the process of WO 01/62232 have been investigated in order to enable incorporation of hydrophobic species. One approach is to add a suitable surfactant into the water-in-oil droplet, which enables dispersion of hydrophobic molecules inside the hydrophilic phase. This is commonly referred to as a multiple emulsion, or double emulsion in this case—specifically an oil/water/oil emulsion. Attempts to apply this approach have been described in a co-pending patent application entitled "Particles Having Hydrophobic Materials Therein" (Kong, Barbe and Finnie)—Australian Provisional Application No. 2005903193.

An alternative approach is to reverse the emulsion and instead use an oil-in-water emulsion (see FIG. 2), which would mean that a hydrophobic species should be able to be contained inside the oil droplets. This would have a considerable advantage industrially because the main solvent is water, which may have important cost and environmental (waste management) advantages. The main challenge using this approach is to design a flexible process that allows a good control over the particle morphology (i.e. size and microstructure) to ensure a high hydrophobic payload as well as a good control over the release of this payload.

Two groups have attempted the encapsulation of actives materials inside silica particles using an oil in water emulsion approach.

Maitra et al, *J. Colloid Interface Sci.* 252, 82-88, (2002) have produced shell structures synthesised by precipitating a silica shell at the surface of ionic micelles. The resulting capsules are loaded by post impregnation with tetraphenyl porphyrin. 60% of the porphyrin was leached from the particles after four hours. This rapid release of the payload is due to the use of an impregnation strategy (i.e. the capsule is formed first and impregnated with the active afterwards) rather than a true encapsulation (i.e. the matrix is formed around the active). In addition, the presence of surfactant composing the micelle forming the core of the capsule helps to solubilize the hydrophobic active and consequently speeds up its release. Furthermore from an application point of view, capsules are fragile and known to rupture easily leading to uncontrolled burst release.

Prasad et al, *J. Am. Chem. Soc.*, 125, 7860-7865 (2003) and published US patent application No. 2004/0180096 entitled "Ceramic based nanoparticles for entrapping therapeutic agents for photodynamic therapy and method of treating same" describe the production of organosilica nanoparticles having an encapsulated photosensitive drug for use in photodynamic therapy. The particles disclosed by Prasad et al are derived from stable micro-emulsions and consequently are in the nanometer range (<100 nm). Although very small particles are of interest for certain applications including drug delivery, their small size usually limits their loading and thus their usefulness. More importantly, Prasad et al disclose that the particles minimise leaching of the drug compound from within the particle such that no significant release of the drug compound takes place. Furthermore the process described by Prasad et al requires the dissolution of the hydrophobic active inside a solvent such as DMF or DMSO, which becomes co-incorporated in the particles. These solvents are known to be very toxic and thus pose significant health and environment problems when released with the actives.

There is therefore a need for a simple and versatile process for incorporating a dopant, such as a hydrophobic material, into solid or gel particles without the need to use toxic solvents. The solid or gel particles having the dopant, e.g. hydrophobic material, therein preferably would be capable of releasing the dopant, e.g. hydrophobic material, under appropriate conditions, and may be capable of doing so at a controllable rate.

OBJECT OF THE INVENTION

It is an object of the present invention to overcome or substantially ameliorate at least one of the above disadvantages. It is a further object to at least partially satisfy the above need.

SUMMARY OF THE INVENTION

Disclosed herein is a process for making particles comprising a hydrophobic material therein, comprising:
 providing an emulsion comprising a continuous hydrophilic phase and a dispersed hydrophobic phase, said hydrophobic phase comprising a precursor material and the hydrophobic material; and
 reacting the precursor material to form the particles comprising the hydrophobic material therein.

In an aspect of the invention there is provided a process for making particles comprising a dopant therein said dopant being releasable from the particles, the process comprising:

providing an emulsion comprising a hydrophilic phase and a hydrophobic phase dispersed in the hydrophilic phase, said hydrophobic phase comprising a precursor material and the dopant; and reacting the precursor material in the presence of a catalyst to form the particles comprising the dopant therein said dopant being releasable from the particles.

The hydrophobic phase may be a discontinuous phase. The hydrophilic phase may be a continuous phase.

The dopant may be a hydrophobic material, or it may be a hydrophilic material, or it may be a material of intermediate hydrophilicity, or it may be a mixture of two or more of these. In one embodiment of the invention, the dopant is a hydrophobic material.

In an aspect of the invention there is provided a process for making particles comprising a hydrophobic material therein said hydrophobic material being releasable from the particles, the process comprising:

providing an emulsion comprising a hydrophilic phase and a hydrophobic phase dispersed in the hydrophilic phase, said hydrophobic phase comprising a precursor material and the hydrophobic material; and reacting the precursor material in the presence of a catalyst to form the particles comprising the hydrophobic material therein said hydrophobic material being releasable from the particles.

In an embodiment of the invention there is provided a process for making particles comprising a hydrophobic material therein, the process comprising: providing an emulsion comprising a continuous hydrophilic phase and a dispersed hydrophobic phase, said hydrophobic phase comprising a precursor material and the hydrophobic material; and reacting the precursor material to form the particles comprising the hydrophobic material therein.

The emulsion may be an oil-in-water (o/w) emulsion. It may be a microemulsion, or may be a different type of emulsion. It may have a mean droplet size between about 1 nm and about 100 microns, between about 100 nm and about 100 microns, between about 100 nm and about 75 microns, between about 100 nm and about 50 microns, between about 100 nm and about 25 microns, between about 100 nm and about 10 microns, between about 100 nm and about 1 micron, between about 100 nm and about 0.75 microns, between about 100 nm and about 0.5 microns, between about 100 nm and about 0.25 microns, between about 200 nm and about 100 microns, between about 200 nm and about 75 microns, between about 200 nm and about 50 microns, between about 200 nm and about 25 microns, between about 200 nm and about 10 microns, between about 200 nm and about 1 micron, between about 200 nm and about 0.75 microns, between about 200 nm and about 0.5 microns, or between about 200 nm and about 0.25 microns. The emulsion may comprise a surfactant, and may be stabilised by the surfactant.

The particles may be solid or gel particles. The particles may comprise a solid matrix.

The precursor material may be any suitable material capable of reacting in the hydrophobic phase of the emulsion to form the particles, or to form the solid matrix. The precursor may be a material that is incapable of reacting with the dopant, e.g. hydrophobic material. The precursor may be hydrophobic. It may be an organosilica precursor, or an organotitania precursor, an organoalumina precursor, an organozirconia precursor, or a mixture of any two, three or four of these. It may be, or comprise, for example, a silane, such as an organosilane. It may be a hydrolysable organosilane or a condensable organosilane. It may be a trialkoxyorganosilane.

The emulsion comprises a catalyst for reaction of the precursor material to form the particles, or to form a solid matrix. The process may comprise the step of adding the catalyst to the emulsion.

The emulsion may be destabilizable, wherein the size of the droplet may change. For example, the emulsion may be destabilised by the addition of the catalyst. In particular, the emulsion may destabilize and the size of the droplet may increase after the addition of the catalyst. For example, the droplet size may be in the order of about 20 nm, e.g., 18 nm, prior to addition of the catalyst, and about 380 nm or more after addition of the catalyst. The final droplet diameter may be from 1.5 to 100 or more, 2 to 90, 3 to 75, 4 to 50, 5 to 30 or 5 to 25 times the size of the initial droplet diameter.

There may be between about 50 and about 99.99% of the precursor material in the hydrophobic phase by weight or volume. The dopant, e.g. hydrophobic material may be an active dopant, e.g. an active hydrophobic material, for example a fluorescent dye, a radiopharmaceutical, a drug, an enzyme, a catalyst, a hormone, a biocide, a flavour, an aroma substance, an oil, a nutraceutical, a vitamin supplement or some other substance, or it may be a mixture of any two or more of these. The dopant, e.g. hydrophobic material, may be distributed, dispersed, immobilised or encapsulated in the particles. There may be between about 0.01% and about 50% of the dopant, e.g. hydrophobic material, in the hydrophobic phase by weight or volume. The ratio of dopant, e.g. hydrophobic material, to precursor material may be between about 1:1 and about 1:5000 or more by weight or volume. The emulsion may comprise between about 1 and 50% hydrophobic phase by weight or by volume.

The step of providing the emulsion may comprise forming the emulsion. This may comprise combining the hydrophobic phase, the hydrophilic phase and a surfactant to form a mixture, and optionally agitating the mixture. The agitating may comprise stirring, swirling, shaking, sonicating or otherwise agitating, and may be vigorous or mild. It may be sufficiently vigorous to form an emulsion. The proportion of the hydrophobic phase in the mixture (or in the emulsion) may be between about 1 and about 50% by weight or by volume, and may be between about 1 and about 20% by weight or by volume. The ratio of surfactant to hydrophilic phase may be between about 1:50 and 1:5 on a weight or volume basis.

The mixture may additionally comprise the catalyst for the reaction of the precursor material to form the particles, or to form the solid matrix. If the precursor material is a trialkoxyorganosilane, the catalyst may be an amine or some other basic catalyst. The catalyst may be soluble in the hydrophobic phase in the emulsion. The catalyst may for example be an aminoorganotrialkoxysilane. The ratio of the catalyst to the precursor material may be between about 3:1 and 0.1:1 or more, on a weight, volume or mole basis. The catalyst may react with the precursor particles. It may be incorporated in the particles. The catalyst may be added after the dopant, e.g. hydrophobic material, has been combined with the precursor material.

The step of reacting the precursor material may comprise maintaining the emulsion for a time and under conditions sufficient for the precursor material to react in the hydrophobic phase, in the presence of the catalyst, if present. The time may be between about 1 minute and 60 hours or more. The conditions may comprise conditions of temperature, and the temperature may be between about 10 and 90° C. The temperature may be a temperature at which the dopant, e.g. hydrophobic material, is stable. It may be a temperature at which the emulsion is stable for the time sufficient for reaction of the precursor material. If the precursor material is condensable, for example a trialkoxyorganosilane, then reaction of the precursor material may comprise condensation thereof. The step of reacting the precursor material may comprise some other means for reacting the precursor material. For example if the precursor material is a radiation crosslinkable material, the step of reacting the precursor material may comprise exposing the emulsion to radiation, e.g. UV, e-beam or γ-radiation. The step of reacting may comprise agitating (e.g. stirring, swirling or shaking) the emulsion during the reacting. The agitating may be for sufficient time to form the particles comprising the dopant, e.g. hydrophobic material, therein. The sufficient time may be for example between about 1 minute and about 60 hours or more, between about 1 minute and 3 hours, between about 1 minute and 2 hours, between about 5 minutes and 3 hours, between about 5 minutes and 2 hours, between about 5 minutes and 1 hour, between about 10 minutes and 3 hours, between about 10 minutes and 2 hours, between about 10 minutes and 1 hour, between about 15 minutes and 3 hours, between about 15 minutes and 2 hours, between about 15 minutes and 1 hour, between about 20 minutes and 3 hours, between about 20 minutes and 2 hours, between about 20 minutes and 1 hour, or between about 1 minute and about 30 minutes.

The process may additionally comprise separating the particles from the hydrophilic phase, and may also comprise washing and/or drying the particles.

In another embodiment there is provided a process for making particles comprising a hydrophobic material therein, comprising:
  providing an emulsion comprising a continuous hydrophilic phase and a dispersed hydrophobic phase, said hydrophobic phase comprising a organotrialkoxysilane, a surfactant, a catalyst for condensation of the organotrialkoxysilane and the hydrophobic material; and
  condensing the organotrialkoxysilane to form the particles comprising the hydrophobic material therein.

In another embodiment there is provided a process for making particles comprising a hydrophobic material therein, comprising:
  combining a hydrophilic phase, a hydrophobic phase and a surfactant, said hydrophobic phase comprising a organotrialkoxysilane, an amine catalyst and the hydrophobic material, to form a mixture, and optionally agitating the mixture, to form an emulsion comprising the hydrophobic phase dispersed in the hydrophilic phase; and
  condensing the organotrialkoxysilane to form the particles comprising the hydrophobic material therein.

In another embodiment there is provided a process for making particles comprising a hydrophobic material therein, comprising:
  combining a hydrophilic phase, a hydrophobic phase and a surfactant, said hydrophobic phase comprising an organotrialkoxysilane and the hydrophobic material, to form a mixture,
  forming an emulsion comprising the hydrophobic phase dispersed in the hydrophilic phase, optionally by agitating the mixture;
  adding a catalyst to the emulsion; and
  condensing the organotrialkoxysilane to form the particles comprising the hydrophobic material therein.

The catalyst may be an amine catalyst. The catalyst may be an aminoorganotrialkoxysilane, for example an aminoalkyltrialkoxysilane. In one embodiment, the catalyst is selected from 3-aminopropyltriethoxysilane (APTES), 3-(2-aminoethylamino)propyltrimethoxysilane (DATMS), 3-aminopropyltrimethoxysilane (APTMS) and 3-[2-(2-aminoethylamino)ethylamino]propyltrimethoxysilane (TATMS). In a particular embodiment the catalyst is APTES. The catalyst may be added after combining the organotrialkoxysilane and the hydrophobic material.

There is also provided a particle having a dopant, e.g. hydrophobic material, therein when made by the process of the invention. The particle may comprise a single particle or an aggregation of particles.

In a second aspect of the invention there is provided a solid particle comprising a dopant, e.g. hydrophobic material, in a solid matrix. The dopant may be a hydrophobic material, or it may be a hydrophilic material, or it may be a material of intermediate hydrophilicity, or it may be a mixture of two or more of these. In one embodiment the dopant is hydrophobic. Other molecules may be attached to or coupled to or coated on the particles of the invention. For example a targeting molecule may be attached to or coupled to or coated on the particles of the invention. The solid matrix may be the product of reaction of a precursor material. The dopant, e.g. hydrophobic material, may be releasable from the solid matrix, and, thereby, from the solid particle. There may be between about 0.01% and about 30%, of the dopant, e.g. hydrophobic material, in the particle by weight or volume. The dopant, e.g. hydrophobic material, may be distributed, dispersed, immobilised or encapsulated in the particle. More than one dopant, e.g. hydrophobic material, may be incorporated in the particles of the invention (e.g. 1, 2, 3, 4, 5, 6, 7, 8, 9, 10 or more dopants). The matrix may comprise a ceramic or a modified ceramic, for example an organically modified ceramic, i.e. a ceramic having bound organic groups. The surface of the particle may be hydrophobic or hydrophilic. The particles may be xerogel particles. The particles may be gel particles. The particle may have a particle size of between about 1 nm and 100 microns, or between about 100 nm and 100 microns. It may be spherical, or it may be some other shape. It may be capable of releasing the dopant, e.g. hydrophobic material, therein, and may be capable of releasing the dopant, e.g. hydrophobic material, at a controlled or predetermined rate. It may be capable of releasing the dopant, e.g. hydrophobic material, over a period of between about 1 minute and 1 month or more. The solid matrix, or the particle, may not have discrete cavities, cells, hollows, compartments or capsules therein. The solid particle, or the matrix, may be non-porous. It may have no significant measurable micro- or mesoporosity. The particles may be in the form of gel particles. The dopant, e.g. hydrophobic material, may be located in the solid matrix such that it is not located in discrete cavities, cells, hollows, compartments or capsules. It may be distributed substantially homogeneously or heterogeneously in the solid matrix. Alternatively the solid matrix or the particle may have a plurality of discrete cavities, cells, hollows, compartments, vacuoles or capsules therein. It may comprise macropores. The dopant, e.g. hydrophobic material, may then be at least partially located, or encapsulated, in the cavities, cells, hollows, compartments, vacuoles or capsules (i.e. macropores). These may be less than about 1 micron in diameter, or less than about 0.5, 0.2, 0.1, 0.05 or 0.01 microns in diameter. They may be between about 0 and about 1 micron in diameter, or between about 0 and 0.05, 0.01 and 1, 0.1 and 1, 0.01 and 0.1, 0.1 and 1, 0.1 and 0.75, 0.1 and 0.5, 0.1 and 0.4, 0.1 and 0.3, 0.15 and 1, 0.15 and 0.75, 0.15 and 0.5, 0.15 and 0.4, 0.15 and 0.3, 0.2 and 1, 0.2 and 0.75, 0.2 and 0.5, 0.2 and 0.4, 0.2 and 0.3, 0.01 and 0.05, 0.5 and 1, 0 and 0.1, 0 and 0.5 or 0.05 and 0.5 microns in diameter, and may be about 0, 0.01, 0.05, 0.1, 0.2, 0.21, 0.22, 0.23, 0.24, 0.25, 0.26, 0.27, 0.28, 0.29, 0.3, 0.4, 0.5, 0.6, 0.7, 0.8, 0.9 or 1 micron in diameter. The diameters of the cells, hollows, compartments or capsules may be monodispersed or polydispersed, and may have a broad distribution.

The solid particle may be made by the process of the first aspect of the invention. The particle having dopant therein, e.g. hydrophobic material therein, may be produced by a sol gel process which may be a process according to the invention.

Hence there is provided a particle comprising a dopant therein said dopant being releasable from the particles, said particle being made by a process comprising:

providing an emulsion comprising a hydrophilic phase and a hydrophobic phase dispersed in the hydrophilic phase, said hydrophobic phase comprising a precursor material and the dopant; and reacting the precursor material in the presence of a catalyst to form the particles comprising the dopant therein said dopant being releasable from the particles.

In a third aspect of the invention there is provided a method for treating a condition in a subject, for example a human, comprising administering to the subject a therapeutically effective quantity of particles according to the present invention, wherein the dopant, e.g. hydrophobic material, of the particles is releasable from said particles and is indicated for the condition. The dopant, e.g. hydrophobic material, may be a drug or some other therapeutic agent. The drug may be an anti-cancer drug. The condition may be a disease. The condition may be for example cancer, AIDS, arthritis, diabetes, hormonal dysfunction, hypertension, pain or some other condition. The condition may be one for which controlled release of a drug or a therapeutic agent is indicated. It may be one for which the drug or therapeutic agent should be dispensed to the subject at a controlled rate. It may be one for which the drug or therapeutic agent is to be dispensed to the subject over an extended period of time.

There is also provided a particle according to the present invention when used for the manufacture of a medicament for the treatment of a condition in a subject, for example a human, wherein the dopant, e.g. hydrophobic material, of the particle is releasable from said particle and is indicated for the condition. The condition may be for example cancer, diabetes, AIDS, hormonal dysfunction, hypertension, pain or some other condition.

There is farther provided the use of particles according to the invention for the treatment of a condition in a subject, for example a human, wherein the dopant, e.g. hydrophobic material, of the particles is releasable from said particles and is indicated for the condition. There is also provided the use of particles of the invention for the manufacture of a medicament for the treatment or prevention of a condition in a subject. The condition may be for example cancer, diabetes, AIDS, hormonal dysfunction, hypertension, pain or some other condition. The particles or compositions may be administered orally, topically, parenterally, for example. The administration may be via a single dose or multiple doses. The particles or compositions may be administered orally, topically, parenterally, for example. The administration may be via a single dose or multiple doses. The dosage of the particles administered will vary and will depend on such as the condition, age and size of the patient as well as the nature of the condition and the dopant, the effectiveness of the dopant, and the amount of dopant encapsulated and released by the particles.

There is also provided a process of making a composition comprising mixing the particles of the invention with an acceptable carrier, diluent, excipient and/or adjuvant. The particles may be in the form of a composition comprising the particles. For parenteral administration, the particles of the invention of suitable size for the intended use may be prepared in sterile aqueous or oleaginous solution or suspension or other suitable solution or suspension. Aqueous solutions or suspensions may further include one or more buffering agents and optionally other suitable additives for the intended purpose.

Depending on the intended purpose, the dosage form of the composition will comprise from 0.005% to 80% by weight or more of the ceramic particles of the invention. Usually, dosage forms according to the invention will comprise from 0.1% to about 25%, more typically 1 to 16% and even more typically 1% to 10% by weight of the particles of the invention.

In a fourth aspect of the invention there is provided a method for delivering a dopant, e.g. hydrophobic material, said method comprising exposing a plurality of particles according to the present invention to a medium capable of releasing the dopant, e.g. hydrophobic material, of the particles, said dopant, e.g. hydrophobic material, being releasable from the particles. The exposing may comprise immersing the particles in the medium, and may additionally comprise one or more of stirring, shaking, swirling or otherwise agitating the medium having the particles therein. Alternatively the exposing may comprise passing the medium past and/or through the particles. The medium may be a fluid, and may be a liquid. The medium may be a biological fluid such as blood. It may be an organic fluid, and may be an organic solvent, for example a hydrophobic solvent, The medium may be capable of dissolving the dopant, e.g. hydrophobic material, and/or of releasing the dopant, e.g. hydrophobic material, from the particles. The medium may be capable of partially or fully dissolving the dopant. The dopant, e.g. hydrophobic material, may be for example an organic compound or substance, fluorescent dye, a radiopharmaceutical, a pharmaceutical substance (a drug), a veterinary substance, an enzyme, a hormone, a biocide, a pesticide, a cosmetic, a herbicide, an agaricide, an insecticide, a fungicide, a flavour, an aroma substance, an oil, a nutraceutical, a vitamin supplement or some other substance, or it may be a mixture of any two or more of these. The medium may be a gas, for example air, and the dopant, e.g. hydrophobic material, may be volatile (for example an aroma material). The exposing may be under conditions suitable for release of the dopant, e.g. hydrophobic material, into the medium. The method may also comprise the step of allowing the dopant, e.g. hydrophobic material, to release into the medium. The method may additionally comprise the step of separating the particles from the medium. The step of separating may comprise filtering, microfiltering, ultrafiltering, centrifuging, ultracentrifuging, settling, decanting, dialysing, or a combination of these. The method for delivering the dopant, e.g. hydrophobic material, may comprise abrading, eroding, dissolving, excoriating, grinding or otherwise removing at least a part of the particle. The abrading etc. may expose the dopant, e.g. hydrophobic material, to the medium.

A further embodiment of the invention provides a method of treating a locus comprising applying particles of the invention or a composition according to the invention to the locus in an amount effective to treat the locus. Another embodiment of the invention provides a method of treating an object comprising administering to the object particles of the invention or a composition according to the invention to the object in an amount effective to treat the object. Yet a further embodiment of the invention provides a method of treating a subject comprising administering to the subject particles of the invention or a composition according to the invention to the subject in an amount effective to treat the subject.

DETAILED DESCRIPTION OF PREFERRED EMBODIMENTS OF THE INVENTION

Figure 1:
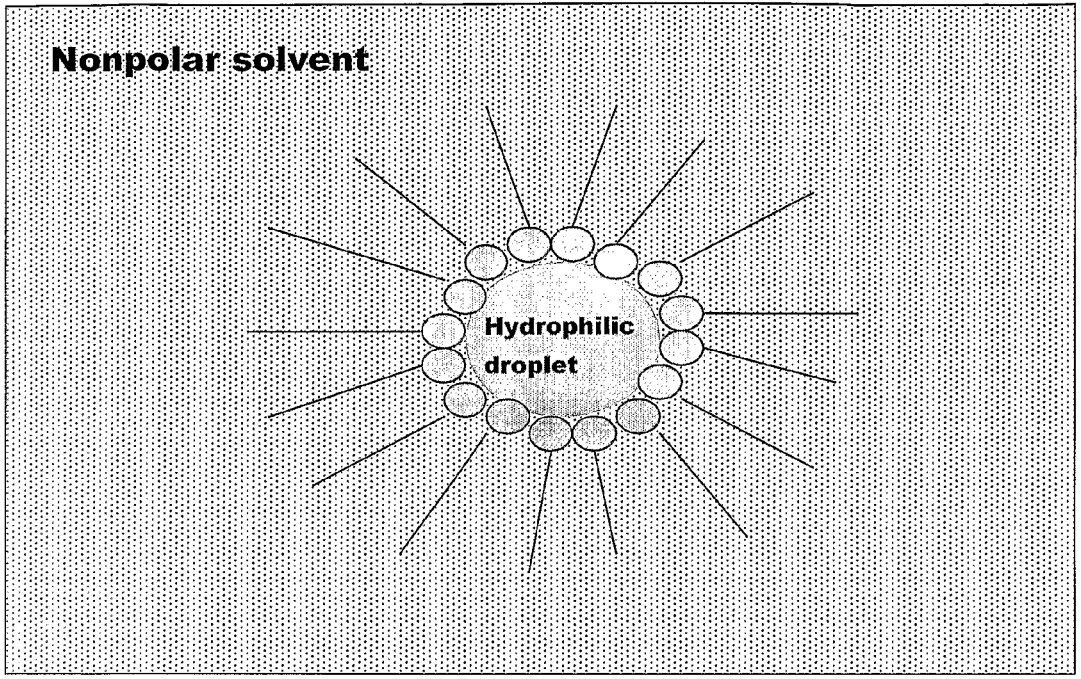
FIG. 1 is a diagrammatic representation of a water-in-oil emulsion system in which sol-gel chemistry is carried out to form silica in the hydrophilic droplet.
Figure 2:
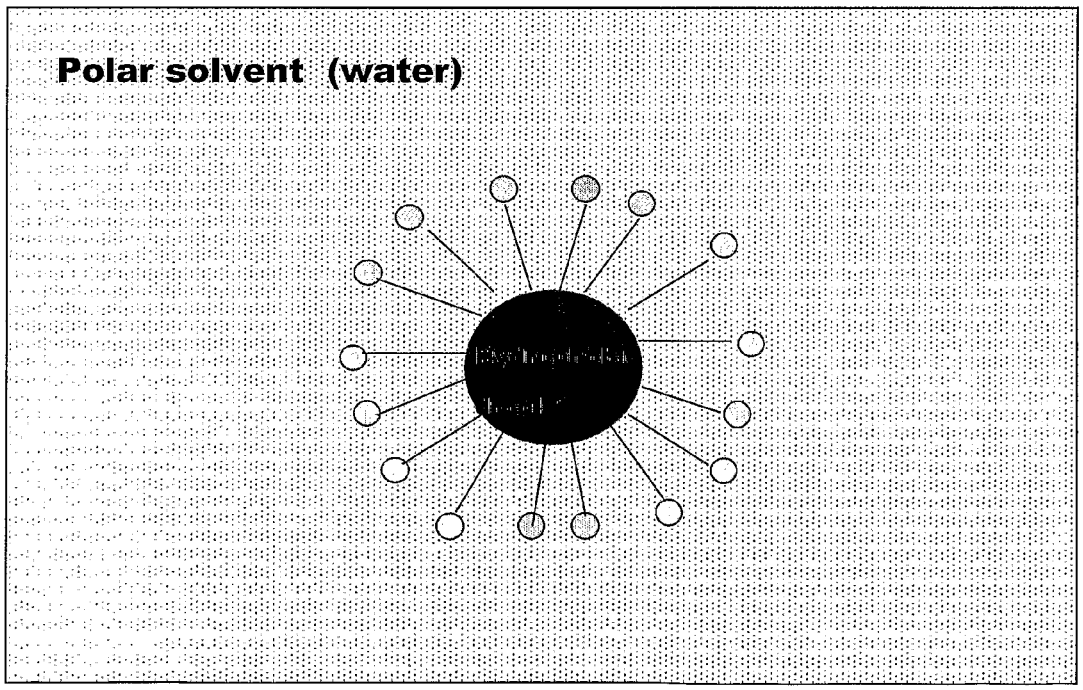
FIG. 2 is a diagrammatic representation of an oil-in-water emulsion system in which sol-gel chemistry is carried out in the hydrophobic droplet.

The present invention relates to particles, including solid particles, having dopants e.g, hydrophobic materials therein, wherein the dopant is for subsequent release from the particle. The invention also relates to processes for preparing such particles. The particles having a dopant encapsulated therein for subsequent release may be used as delivery vehicles of active agents such as drugs, dyes, radiopharmaceuticals and the like.

In the present invention, the problem of keeping a precursor material (or partial reaction products thereof) in the hydrophobic phase during the sol-gel reaction is addressed by chemical modification of the precursor. Although the typical alkoxides (tetramethoxysilane, tetraethoxysilane) used in related processes are hydrophobic, as the hydrolysis reaction proceeds, resulting in replacement of the alkoxide groups with hydroxyl (silanol) groups, the species becomes more hydrophilic and miscible with the continuous hydrophilic phase. In order to keep the precursor material located in the hydrophobic phase throughout the process, an organically modified silane ("ormosil") may be used in which one alkoxide group of a tetraalkoxysilane has been replaced by an organic group, such as a phenyl group ($C_6H_5$—) to produce an organotrialkoxysilane. This organic fragment cannot be cleaved from the central silicon atom during the hydrolysis reaction and thus 'anchors' the silicon species inside the hydrophobic domain. The resulting product is not, however, silica, but a modified version, referred to here as organosilica, where the 'organo' depends on the species used to replace the alkoxide.

Conduction of the sol-gel reaction inside the hydrophobic droplet is more problematic, because sol-gel chemistry is typically hydrolytic (i.e. involves water). Non-hydrolytic sol-gel is a specialised branch of sol-gel chemistry, but typically involves reagents incompatible with water (such as $SiCl_4$), catalysts, and high temperatures in order to get the reactions to proceed. As the inventors specifically want to use an aqueous continuous hydrophilic phase, this approach has been avoided. Instead, 3-aminopropyltriethoxysilane (APTES) was used to catalyse the hydrolysis and condensation of an organo-silicon species, as described by Ottenbrite et al. [Ottenbrite, R. M., Wall, J. S., Siddiqui, J. A., *J. Am. Ceram. Soc.*, 83 (12) 3124-3125, (2000); Wall, J. S., Hu, B., Siddiqui, J. A., Ottenbrite, R. M., *Langmuir*, 17 (19), 6027-6029, (2001)]. The mechanism for this reaction is not well-understood; however, it appears that APTES may act to catalyse the condensation reaction and also may be incorporated in the product to some extent, resulting in an amine-functionalized surface. The dopant, e.g. hydrophobic material, may be added before, at the same time as (e.g. as a mixture with) or after the organosilicon species. However the dopant, e.g. hydrophobic material, should be added before addition of APTES.

Thus the present specification describes a process for producing particles comprising a dopant, e.g. hydrophobic material, therein, and formed by having the dopant, e.g. hydrophobic material, dispersed inside the oil droplets of an oil-in-water emulsion, prior to addition of the APTES. The particles obtained generally are nanosized, with a wider size range than the typical base-catalysed silicas. A number of hydrophobic molecules—solvent blue and sudan red dyes, limonene, diuron and retinol—have been incorporated into particles. Incorporation of a hydrophilic dopant has also been demonstrated.

According to the present invention there is provided a process for making particles comprising a dopant, e.g. hydrophobic material, therein. The process comprises providing an emulsion comprising a continuous hydrophilic phase and a dispersed hydrophobic phase, in which the hydrophobic phase comprises a precursor material and a dopant, e.g. hydrophobic material, and may also comprise a catalyst for reaction of the precursor material to produce the particles. The precursor material is then reacted within the dispersed phase of the emulsion to form the particles. The reaction may be a polymerisation, a condensation, a solidification, a crosslinking or some other reaction, or some combination of these. As the precursor material reacts to form the particles, the dopant, e.g. hydrophobic material, in the precursor material becomes incorporated or encapsulated in the particles, thus reaction of the precursor material forms the particles comprising the dopant, e.g. hydrophobic material, therein. The dopant may be added in the absence of a solvent other than a surfactant. The dopant may be added as a solution, or micellar solution, in a surfactant.

During reaction of the precursor material to produce the particles, the size of the emulsion droplets, in which the particles form during said reaction, commonly increases. For example, the size may increase by at least 50, 60, 70, 80, 90, 100, 130, 150, 170, 200, 230, 250, 280, 300, 330, 350, 380, 400, 430, 450, 480, 500, 700, 800, 900, 1000, 1300, 1500, 1700, 2000, 3000, 4000, 5000% or more, or between about 50 and about 5000% or more, or between about 50 and about 4000%, or between about 50 and about 3000%, or between about 50 and about 2000%, or between about 50 and about 1500%, or between about 50 and about 1000%, or between about 50 and 250, 50 and 100, 100 and 500, 250 and 500, 100 and 300 or 100 and 200%, e.g. about 50, 100, 15, 200, 250, 300, 350, 400, 450 or 500%. The size of the droplets may be equated with the diameter of the droplets.

The size increase may comprise swelling, agglomeration, Ostwald ripening or some other form of size increase. Thus the process may comprise the step of increasing the size of the droplets of the dispersed hydrophobic phase.

In the present invention, various steps of agitation are or may be used. The method employed for these steps is not critical and any commonly used agitation equipment, such as a blade or paddle mixer, mechanical stirrer, magnetic stirrer etc. is suitable. For high shear agitation, a sonicator may also be used.

The emulsion may be an oil-in-water emulsion, and may comprise droplets of the hydrophobic phase dispersed in the hydrophilic phase. The emulsion may have a mean droplet size between about 1 nm and about 100 microns, or between about 1 nm and 10 microns, 1 nm and 1 micron, 1 and 100 nm, 1 and 50 nm, 50 nm and 10 microns, 100 nm and 100 microns, 100 nm and 50 microns, 100 nm and 10 microns, 500 nm and 10 microns, 1 and 10 microns, 5 and 10 microns, 50 and 50 nm, 100 nm and 1 micron, 100 and 500 nm, 10 and 100 microns, 1 and 100 microns, 10 and 50 microns, 50 and 100 microns or 500 nm and 1 micron, and may have a mean droplet size of about 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800 or 900 nm or about 1, 1.5, 2, 2.5, 3, 3.5, 4, 4.5, 5, 6, 7, 8, 9, 10, 15, 20, 25, 30, 35, 40, 45, 50, 60, 70, 80, 90 or 100 microns, or may have a mean droplet size greater than about 100 microns.

The hydrophilic phase may comprise water, and may be an aqueous phase. It may comprise a hydrophilic solvent, e.g. water. It may comprise one or more salts or other additives. It may for example comprise sodium chloride, potassium chloride, calcium chloride or some other salt. The concentration of the salt may be any concentration up to the saturation concentration of the salt in the hydrophilic phase. It may be for example about 5, 10, 15, 20, 25, 30, 35, 40, 45, 50, 55, 60, 65, 70, 75, 80, 85, 90, 95 or 100% of the saturation concentration of the salt in the hydrophilic phase. For example if the salt is sodium chloride the concentration may be up to about 2 mol/L. The salt may be useful during freeze drying or storage of the particles.

The precursor material may be any suitable material to form the solid matrix, or the particles. In a particular embodiment, the precursor material may be capable of remaining in the hydrophobic phase of the emulsion. Generally, the precursor material is sufficiently non-polar as to partition preferentially into the hydrophobic phase. If the precursor material is hydrolysable, it may be sufficiently non-polar that a hydrolysis product thereof is capable of remaining in the hydrophobic phase, at least before addition of the condensation catalyst. The precursor material, and optionally also a hydrolysis product thereof, may be insoluble, or sparingly soluble, or very sparingly soluble, in the hydrophilic phase. It may comprise a precursor to a ceramic, i.e. a ceramic precursor. The ceramic may be an organosilica, an organozirconia, an organoalumina or an organotitania, or a mixture of two, three or four of these, or an organically modified (i.e. substituted) mixed metal oxide. The precursor material may comprise a silicon species or some other metal species, where the metal may be for example aluminium, zirconium (e.g. an organozirconate) or titanium (e.g. an organotitanate), or it may comprise a mixture of such species. The precursor material may comprise, or be mixed with, other additives, e.g. condensable additives, such as zirconates, organoaluminium compounds, titanates and/or silanes that do not bear non-hydrolysable organic groups but which can condense with the precursor material. The precursor material may comprise for example a silane. A suitable silane may comprise three hydrolysable groups attached to a silicon atom. This enables it to crosslink by condensation. The silane may also have an organic group attached to the silicon atom. This may render the silane sufficiently hydrophobic as to partition preferentially into the hydrophobic phase. Suitable hydrolysable groups include alkoxy groups OR, where R is a straight chain, branched chain or cyclic alkyl group. The alkyl group may have between about 1 and 18 carbon atoms, or between 1 and 12, 1 and 6, 1 and 4, 6 and 18, 12 and 18 or 6 and 12 carbon atoms, and may have 1, 2, 3, 4, 5, 6, 7, 8, 9, 10, 11, 12, 13, 14, 15, 16, 17 or 18 carbon atoms. It may have between 0 and 4 side chains, for example, 0, 1, 2, 3 or 4 side chains. Thus the alkoxy group may be for example methoxy, ethoxy, propoxy, isopropoxy, butoxy, isobutoxy, pentoxy, hexyloxy, octyloxy, isooctyloxy, decyloxy, dodecyloxy, cetyloxy, stearyloxy, cyclohexyloxy or cyclopentyloxy. The silicon atom of the silane may have different hydrolysable groups attached thereto, for example more than one of the above mentioned groups. Also, it will be understood that many of the above groups are derived from natural sources (e.g. stearyloxy is derived from stearic acid, derived from animal fats or plant oils), and that these may be present as mixtures of chain lengths, e.g. "stearyloxy" may also comprise lesser amounts of C16, C14 and/or C20 chains as well as C18 chains. The above groups may be substituted (e.g. with functional groups, halogens, aryl groups etc.) or may be unsubstituted. Other suitable hydrolysable groups include aryloxy, which may have between about 6 and 14 carbon atoms, and may have for example, 6, 8, 10, 12 or 14 or more than 14 carbon atoms. Examples include phenoxy, biphenyloxy, naphthyloxy and anthracyloxy. These may each, optionally, be substituted by one or more alkyl groups (e.g. C1 to C6 straight chain or branched alkyl), halogens, functional groups or other substituents. Suitable organic groups attached to the silicon atom of the silane include alkyl groups, for example C1 to C12 straight chain, branched chain or cyclic alkyl. Other suitable hydrolysable groups include alkenyloxy (e.g. isopropenyloxy), benzoyloxy, benzamido, oximo (e.g. methylethylketoximo) or other hydrolysable groups known in the art.

Suitable alkyl groups attached to the silicon atom of the silane include for example ethyl, propyl, isopropyl, butyl, isobutyl, tert-butyl, pentyl, hexyl, isooctyl, decyl, dodecyl, cyclohexyl, cylcooctyl or cyclopentyl. These may be substituted (e.g. with functional groups, halogens, aryl groups etc.) or may be unsubstituted. Other suitable organic groups include aryl groups, which may have between about 6 and 14 carbon atoms, and may have for example, 6, 8, 10, 12 or 14 or more than 14 carbon atoms. Examples include phenyl, biphenyl, naphthyl and anthracyl. These may each, optionally, be substituted by one or more alkyl groups (e.g. C1 to C6 straight chain or branched alkyl), halogens, functional groups or other substituents. The silicon atom of the silane may have an alkenyl or alkynyl or benzyl group attached to it. The alkenyl or alkynyl group may have between 2 and about 18 carbon atoms, and may be straight chain, branched or (if sufficient carbon atoms are present) cyclic. It may have 1 or more than 1 double bond, or 1 or more than 1 triple bond, and may have a mixture of double and triple bonds. If the group has more than one unsaturated group, the unsaturated groups may be conjugated or unconjugated.

Suitable silanes include ethyl trimethoxysilane, vinyltrimethoxysilane, phenyltrimethoxysilane, isopropyltrimethoxysilane, benzyltrimethoxysilane, ethyltriethoxysilane, vinyltriethoxysilane, phenyltriethoxysilane, isopropyltriethoxysilane and benzyltriethoxysilane.

Other suitable precursors may comprise siloxane dimers or trimers, provided that, when mixed with the other components of the hydrophobic phase to form the hydrophobic phase at the temperature at which the emulsion is formed, the hydrophobic phase is a liquid. The temperature at which the emulsion is formed may be between about 10 and 90° C., or between about 10 and 80, 10 and 60, 10 and 40, 10 and 20, 20 and 90, 40 and 90, 60 and 90, 20 and 70, 20 and 50 or 20 and 30° C., and may be about 10, 15, 20, 25, 30, 35, 40, 45, 50, 55, 60, 65, 70, 75, 80, 85 or 90° C., or may be greater than about 90° C. or less than about 10° C. It may be the same temperature as the temperature at which the precursor is reacted to form the solid matrix, or it may be a different temperature. The siloxane dimers or trimers may have at least three hydrolysable groups per molecule, and the hydrolysable groups may be the same as those described earlier for the silane. They may also comprise at least one organic group attached to a silicon atom, and the organic groups may be as described earlier for the silane. Suitable siloxane dimers or trimers may include tetramethoxydiphenyldisiloxane, tetramethoxydivinyldisiloxane, tetraethoxydiphenyldisiloxane, tetraethoxydivinyldisiloxane, tetramethoxydioctyldisiloxane, tetraethoxydioctyldisiloxane, pentamethoxytriphenyltrisiloxane, pentaethoxytriphenyltrisiloxane, pentamethoxytrivinyltrisiloxane, pentaethoxytrivinyltrisiloxane, pentamethoxytrioctyltrisiloxane and pentaethoxytrioctyltrisiloxane.

Mixtures of any of the above described silanes, siloxane dimers and siloxane trimers, together, optionally, with other substances that can cocondense or copolymerise with these, may also be used.

The emulsion may also comprise a catalyst for solidification of the hydrolysed precursor material. This may be an amine. The amine may be capable of partitioning into the dispersed hydrophobic phase. The catalyst may be an aminofunctional silane. It may for example be an aminoalkyl trialkoxysilane (including a monoaminoalkyl trialkoxysilane, a diaminoalkyl trialkoxysilane and a triaminoalkyl trialkoxysilane). It may have formula X—R'—Si(OR)$_3$, in which OR is a hydrolysable group, R' is an alkylene group, and X is an amine functionality (e.g. NH$_2$, NHR", NR"$_2$, H$_2$NCH$_2$CH$_2$NH etc. where R" is an alkyl or aryl group, for example methyl, ethyl, propyl or cyclohexyl). R' may have between 1 and 6 or more than 6 carbon atoms, and may have for example 1, 2, 3, 4, 5 or 6 carbon atoms. One or more the carbon atoms comprising R' may be mono- or di-substituted with X. Suitable aminoalkyltrialkoxysilanes include 3-aminopropyltrimethoxysilane, 3-(2-aminoethylamino)propyltrimethoxysilane, 3-aminopropyltriethoxysilane and 3-[2-(2-aminoethylamino)ethylamino]propyltrimethoxysilane. The catalyst may comprise a compound having hydrophilic groups (for example the amines described above). There may be sufficient catalyst that the surfaces of the particles made by the process are hydrophilic, or sufficiently hydrophilic that the particles are capable of dispersing in water, or that the surfaces of the particles may be wetted by water. The catalyst may be a surfactant, for example an aminosurfactant. The ratio of catalyst to precursor may be between about 2:1 and 0.01:1, or between about 2:1 and 0.1:1, 2:1 and 0.5:1, 1:1 and 0.01:1, 1:1 and 0.1:1, 1:1 and 0.5:1, 0.1:1 and 0.01:1, 0.5:1 and 0.1:1, 0.8:1 and 1:0.8, 0.9:1 and 1:0.9, 0.95:1 and 1:0.95, 0.98:1 and 1:0.98 or 1:1 and 0.5:1, and may be about 2:1, 1.5:1, 1.4:1, 1.3:1, 1.2:1, 1.15:1, 1.1:1, 1.05:1, 1:1, 1:1.05, 1:1.1, 1:1.15, 1:1.2, 1:1.3, 1:1.4, 1:1.5, 0.9:1, 0.8:1, 0.7:1, 0.6:1, 0.5:1, 0.4:1, 0.3:1, 0.2:1, 0.1:1, 0.05:1 or 0.01:1 on a w/w, w/v, v/v or mole basis. The catalyst catalyses the precursor condensation. The catalyst may be soluble in the hydrophobic phase of the emulsion. From a practical point of view, although some organic amines do fulfill these criteria the product yield obtained with them is very low. In the case of silica particles or Si containing particles the preferred catalyst is amino-siloxane or amino hydrolysable silane which is incorporated in the silica network in the particles as they are made by the process of the invention. The emulsion may be destabilized on addition of the catalyst. The catalyst may be an amino hydrolysable aluminate, amino hydrolysable zirconate or an amino hydrolysable titanate in the case Al, Zr or Ti containing particles respectively.

The amino content of the particles may be between 5 and 25 mol %, 7 and 23 mol %, 9 and 21 mol %, 11 and 19 mol %, or between 13 and 17 mol %. The amino content of the particles (as determined by CHN analysis) may be between 5 and 25 mol %, 7 and 23 mol %, 9 and 21 mol %, 11 and 19 mol %, or between 13 and 17 mol %. The amino content of the particles may be about 5, 6, 7, 8, 9, 10, 11, 12, 13, 14, 15, 16, 17, 18, 19, 20, 21, 22, 23, 24, 25 or more mol %.

The hydrophobic phase of the emulsion used in the process for making the particles of the present invention may have between about 50 and 99.99% of the precursor material by weight or volume. It may have between about 50 and 95, 50 and 90, 50 and 80, 50 and 70, 50 and 60, 60 and 95, 70 and 95, 70 and 90, 70 and 80, 70 and 99.99, 90 and 99.99, 99 and 99.99 or 99.9 and 99.99% of the precursor material in the emulsion, and may have about 50, 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8, 99.9, 99.95 or 99.99% by weight or by volume. There may be between about 0.01% and 50% of the dopant, e.g. hydrophobic material, in the hydrophobic phase by weight or volume, or between about 0.01 and 40, 0.01 and 30, 0.01 and 20, 0.01 and 10%, 0.01 and 1%, 0.01 and 0.5%, 0.01 and 0.1%, 0.01 and 0.05%, 0.1 and 30%, 1 and 30%, 5 and 30%, 1 and 50, 10 and 50, 20 and 50, 30 and 50, 20 and 40, and 40, 30 and 35, 10 and 30%, 0.1 and 10%, 0.1 and 1% or 1 and 10% by weight or volume, and may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45 or 50% by weight or volume. The ratio of dopant, e.g. hydrophobic material, to precursor material may be between about 1:1 and about 1:5000 or more by weight or volume, and may be between about 1:1 and 1:1000, 1:1 and 1:100, 1:1 and 1:10, 1:1 and 1:5, 1:1 and 1:2, 1:2 and 1:5000, 1:2 and 1:1000, 1:2 and 1:500, 1:2 and 1:100, 1:2 and 1:50, 1:2 and 1:10, 1:2 and 1:5, 1:10 and 1:5000, 1:100 and 1:1000, 1:1000 and 1:5000, 1:10 and 1:1000, 1:10 and 1:100 or 1:100 and 1:1000, and may be about 1:1, 1:2, 1:3, 1:4, 1:5, 1:6, 1:7, 1:8, 1:9. 1:10, 1:20, 1:50, 1:100, 1:200, 1:500, 1:1000, 1:2000, 1:3000, 1:4000 or 1:5000 by weight or by volume. The emulsion may comprise between about 1 and about 50% hydrophobic phase by weight or by volume, or between about 1 and 25, 1 and 20, 1 and 15 1 and 10, 1 and 5, 5 and 50, 10 and 50, 25 and 50 or 10 and 25% hydrophobic phase, and may comprise about 1, 2, 3, 4, 5, 6, 7, 8, 9, 10, 15, 20, 25, 30, 35, 40, 45 or 50% hydrophobic phase by weight or by volume. The ratio of precursor material to hydrophilic phase may be between about 1:50 and 1:5, or between about 1:50 and 1:10, 1:50 and 1:20, 1:20 and 1:5, 1:10 and 1:5, 1:25 and 1:10 or 1:30 and 1:20, and may be about 1:50, 1:40, 1:30, 1:25, 1:20, 1:15, 2:25, 1:10 or 1:5 on a w/w or w/v basis.

The emulsion, in particular the hydrophobic phase of the emulsion, may be stabilised by a surfactant. The ratio of surfactant to hydrophilic phase may be between about 1:50 and 1:5, or between about 1:50 and 1:10, 1:50 and 1:20, 1:20 and 1:5, 1:30 and 1:15, 1:25 and 1:15, 1:15 and 1:5 or 1:20 and 1:10, and may be about 1:50, 1:40, 1:30, 1:20, 1:15, 1:10, 1:9, 1:8, 1:7, 1:6 or 1:5 on a w/w or w/v basis.

The surfactant may be any surfactant capable of dissolving the dopant. The surfactant may have an HLB (hydrophilic/lipophilic balance) between about 10 and 20, or between about 10 and 15, 10 and 14, 10 and 13, 15 and 20, 15 and 18, 12 and 15, 12 and 14 or 12 and 13, and may have an HLB of about 10, 11, 12, 13, 14, 15, 16, 17, 18, 19 or 20. The surfactant may be cationic, anionic, non-ionic or zwitterionic. It may be for example an alkylphenol ethoxylate, an alkyl (straight or branched chain) alcohol ethoxylate, an ethylene oxide-propylene oxide copolymer or some other type of surfactant. Suitable alkylphenolethoxylates may have alkyl groups between 6 and 10 carbon atoms long, for example 6, 7, 8, 9 or 10 carbon atoms long, and may have an average number of ethoxylate groups between about 7 and 12, or between about 8 and 10, for example about 7, 8, 9, 10, 11 or 12. The surfactant may, when dispersed or dissolved in water at a weight ratio of 1:20, have a pH of between about 3.5 and 7, or between about 4 and 6, 4 and 5, 5 and 6 or 6 and 7, or about 3.5, 4, 4.5, 5, 5.5, 6, 6.5 or 7. Suitable surfactants include PEG-9 nonyl phenyl ether (eg. NP-9), PEG-9 octyl phenyl ether (eg. Triton X-100) or PEG-8 octylphenyl ether (eg. Triton X-114). The surfactant may be capable of combining, for example copolymerising or co-crosslinking, with the precursor material. If the precursor material has trialkoxysilyl functionality, the surfactant may also have trialkoxysilyl functionality. For example the surfactant may be of formula $R^1SiOR^2(OR^3)(OR^4)$, in which $R^1$ is a polar group, and $R^2$, $R^3$ and $R^4$ may be the same or different, and at least one of $R^2$, $R^3$ and $R^4$ is a long chain alkyl group. At least one of $R^2$, $R^3$ and $R^4$ may have between about 6 and 18 carbon atoms, or between about 6 and 12, 12 and 18, 8 and 18 or 8 and 16 carbon atoms, and may have 6, 7, 8, 9, 10, 11, 12, 13, 14, 15, 16, 17 or 18 carbon atoms, or more than 18 carbon atoms.

In order to form the emulsion, the hydrophilic phase and the hydrophobic phase, and optionally a surfactant are combined to form a mixture. The ratios of hydrophilic phase, hydrophobic phase, and surfactant that are combined to form the mixture are the same as the ratios of those components in the emulsion, as set out above. It will be understood by those skilled in the art that different orders of addition may be used to form the emulsion. Thus the hydrophilic and hydrophobic phases may be combined, and the surfactant may then be added. Alternatively the surfactant may be combined with the hydrophobic phase and the hydrophilic phase then added. It may be necessary to agitate the mixture in order to form the emulsion. The agitation may be vigorous or mild. The agitation may comprise high shear or low shear or medium shear. It may comprise mixing, stirring, swirling, shaking, sonicating, ultrasonicating or some other manner of agitating, or may comprise a combination of these.

After the emulsion has been formed, the precursor, or the hydrophobic phase, may be reacted to form the solid matrix, or to form the particles. This may comprise maintaining the emulsion for a time and under conditions sufficient for the precursor material to react in the hydrophobic phase. The time may depend on the nature of the precursor, the presence or absence of catalyst, on the nature of the catalyst (if present), on the intensity and wavelength of radiation used to cause the precursor material to react (if radiation is used), on the temperature of the emulsion and on other parameters. The time may be greater than about 1 minute, or greater than about 1, 2, 3, 4, 5, 6, 7, 8, 9, 10, 11, 12, 18, 24, 36, 48 or 60 hours, or between about 1 minute and about 60 hours, or may be more than about 60 hours or less than about 1 minute or less than about 5, 10, 15, 20, 25, 30, 35, 40, 45, 50, 55 or 60 minutes. The time may be between about 1 minute and 24 hours, 1 minute and 10 hours, 1 minute and 1 hour, 1 and 30 minutes, 1 and 10 minutes, 1 and 5 minutes, 1 and 60 hours, 3 and 60 hours, 4 and 60 hours, 7 and 60 hours, 10 and 60 hours, 24 and 60 hours, 30 and 60 hours, 30 minutes and 30 hours, 1 and 24 hours, 3 and 24 hours, 4 and 24 hours, 7 and 24 hours, 12 and 24 hours or 1 and 12 hours, and may be about 1, 2, 3, 4, 5, 10, 15, 20, 25, 30, 35, 40, 45, 50 or 55 minutes, or about 1, 1.5, 2, 2.5, 3, 3.5, 4, 4.5, 5, 5.5, 6, 6.5, 7, 7.5, 8, 9, 10, 11, 12, 15, 18, 21, 24, 30, 36, 42, 48, 54 or 60 hours. The time may depend on the nature of the precursor material, the temperature, the nature and concentration of catalyst and on other factors. The temperature, and other reaction conditions, may be selected in order not to adversely affect the dopant, e.g. hydrophobic material. For example it may be selected not to cause the dopant, e.g. hydrophobic material, to decompose or denature. It may optionally be selected not to cause the dopant, e.g. hydrophobic material, to become soluble in the hydrophilic phase or to volatilise. The temperature may also be selected so as not to cause other components (e.g. the precursor material, the hydrophilic phase or the surfactant) to decompose or 10 denature, or to boil or freeze. It may be selected so that the emulsion is stable for the time sufficient for reaction of the precursor material at the temperature. It may be between about 10 and 90° C., or between about 10 and 80, 10 and 60, 10 and 40, 10 and 20, 20 and 90, 40 and 90, 60 and 90, 20 and 70, 20 and 50 or 20 and 30° C., and may be about 10, 15, 20, 25, 30, 35, 40, 45, 50, 55, 60, 65, 70, 75, 80, 85 or 90° C., or may be greater than about 90° C. or less than about 10° C.

The process may additionally comprise separating the particles from the hydrophilic phase, and may also comprise washing and/or drying the particles. The step of separating the particles may comprise filtering, microfiltering, ultrafiltering, centrifuging, ultracentrifuging, settling, decanting, dialysing, or a combination of these. The particles may then be washed. The washing may be with water, or an aqueous solution, or the aqueous phase or with some other suitable washing liquid. It is preferably with a washing liquid that does not release the dopant, e.g. hydrophobic material, from the particles. There may be one or more than one step of washing, for example 2, 3, 4, 5, 6, 7, 8, 9 or 10 steps, or the particles may not be washed. The washing may be sufficient to remove unbound surfactant from the particles. Each step of washing may use the same washing liquid, or may use a different washing liquid. Each step of washing may comprise suspending the particles in the washing liquid, optionally agitating the particles in the washing liquid, and at least partially separating the particles from the washing liquid. Alternatively any or all of the steps of washing may comprise passing the washing liquid through or past or over the particles, under the force of gravity, vacuum, centrifugation or some other force, for example in a filter funnel, a Buchner funnel, a centrifugal separator or some other suitable device. If centrifuging is used, the speed may be between about 1000 and about 25000 rpm, or between about 1000 and 10000, 1000 and 5000, 5000 and 25000, 10000 and 25000, 15000 and 25000, 5000 and 15000, 8000 and 12000, 9000 and 11000 or 9500 and 10500 rpm. It may be greater than about 1000, 5000, 9000, 10000, 15000, 20000 or 25000 rpm. It may be about 1000, 2000, 3000, 4000, 5000, 6000, 7000, 8000, 9000, 1000, 11000, 12000, 15000, 20000 or 25000 rpm.

The particles may be dried. The step of drying may comprise heating the particles. The heating may be to a temperature below the temperature at which the dopant, e.g. hydrophobic material, vaporises, evaporates, sublimes, decomposes or deteriorates, and may be for example between about 30 and 80° C., or between about 30 and 60, 30 and 40, 40 and 80, 60 and 80 or 40 and 60° C., and may be about 30, 35, 40, 45, 50, 55, 60, 65, 70, 75 or 80° C., or may be greater than 80° C. Alternatively or additionally the step of drying may comprise freeze-drying, for example as described in W01/62332 (Barbe and Bartlett, "Controlled Release Ceramic Particles, Compositions thereof, Processes of Preparation and Methods of Use"), the contents of which are incorporated herein by cross-reference. The step of drying may additionally or alternatively comprise passing a stream of gas over and/or through the particles. The gas may be a gas that is inert to the particles and to the dopant, e.g. hydrophobic material, and may be for example air, nitrogen, argon, helium, carbon dioxide or a mixture of these, and may be dried. The step of drying may additionally or alternatively comprise applying a partial vacuum to the particles. The partial vacuum may have an absolute pressure of for example between about 0.01 and 0.5 atmospheres, or between about 0.01 and 0.1, 0.01 and 0.05, 0.1 and 0.5, 0.25 and 0.5, 0.05 and 0.1 or 0.1 and 0.25 atmospheres, and may have an absolute pressure of about 0.01, 0.05, 0.1, 0.2, 0.3, 0.4 or 0.5 atmospheres.

The process of making the particles as described herein may result in an encapsulation efficiency (i.e. an incorporation efficiency: the amount of dopant, e.g. hydrophobic material, in the particles produced by the process as a proportion of the amount of dopant, e.g. hydrophobic material, used in the process) of between about 5 and 95%, or between about 5 and 50, 5 and 20, 10 and 95, 50 and 95, 10 and 50 or 20 and 80%, and may be about 5, 10, 15, 20, 25, 30, 35, 40, 45, 50, 55, 60, 65, 70, 75, 80, 85, 90 or 95%, or more than 95%, depending on the nature of the precursor, the nature of the dopant, e.g. hydrophobic material, the conditions used to make the particles and the method used to determine the efficiency.

The features described throughout the specification or claims for the process of the invention may be present in any workable combination of process steps.

The particles of the present invention comprise the dopant, e.g. hydrophobic material in a solid matrix. The hydrophobic material may be a hydrophobic molecule, for example. The solid matrix may be the product of reaction of the precursor material. It may be a polymerisation and/or condensation and/or crosslinking product of the precursor material or some other reaction product of the precursor material. It may be a hydrolysed silane, such as a hydrolysed organosilane. It may comprise an organically modified ceramic, such as an organically modified silica (organo-silica). It may be a ceramic having bound organic groups. The bound organic groups may be ethyl, propyl, isopropyl, butyl, isobutyl, tert-butyl, pentyl, hexyl, isooctyl, decyl, dodecyl, cyclohexyl, cylcooctyl or cyclopentyl. These may be substituted (e.g. with functional groups, halogens, aryl groups etc.) or may be unsubstituted. Other suitable organic groups include aryl groups, which may have between about 6 and 14 carbon atoms, and may have for example, 6, 8, 10, 12 or 14 or more than 14 carbon atoms. Examples include phenyl, biphenyl, naphthyl and anthracyl. These may each, optionally, be substituted by one or more alkyl groups (e.g. C1 to C6 straight chain or branched alkyl), halogens, functional groups or other substituents. The organic group may be an alkenyl or alkynyl or benzyl group. The alkenyl or alkynyl group may have between 2 and about 18 carbon atoms, and may be straight chain, branched or (if sufficient carbon atoms are present) cyclic. It may have 1 or more than 1 double bond, or 1 or more than 1 triple bond, and may have a mixture of double and triple bonds. If the group has more than one unsaturated group, the unsaturated groups may be conjugated or unconjugated. The solid matrix may comprise chemical groups derived from the catalyst, and the groups may be on the surface of the particles. If the surfactant is capable of combining chemically with the precursor material, the matrix may comprise chemical groups derived from the surfactant. For example if the precursor material comprises an organotrialkoxysilane, and the catalyst comprises a trialkoxyaminoalkylsilane, then the matrix may comprise aminoalkylsilyl units. These may be distributed evenly or unevenly through the particle. They may be preferentially near the surface of the particle. They may provide some degree of hydrophilicity, e.g. due to amino functionality, to the particle surface. Additionally, the surfactant may be capable of combining chemically with the precursor material. For example if the precursor material comprises an organotrialkoxysilane, and the surfactant comprises trialkoxysilyl functionality, then the matrix may comprise surfactant derived units. The surfactant may be adsorbed on the surface of the particle.

The dopant, e.g. hydrophobic material, may represent between about 0.01 and 30% of the weight or the volume of the particle, or between about 0.01 and 10%, 0.01 and 1%, 0.01 and 0.5%, 0.01 and 0.1%, 0.01 and 0.05%, 0.1 and 30%, 1 and 30%, 5 and 30%, 10 and 30%, 0.1 and 10%, 0.1 and 1% or 1 and 10% of the weight or the volume of the particle, and may represent about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25 or 30% of the weight or the volume of the particle. The dopant, e.g. hydrophobic material, may be capable of being released from the particle. The dopant, e.g. hydrophobic material, may be capable of being released from the particle over a period of time. The dopant, e.g. hydrophobic material, may be capable of being released from the particle over a period of time at a controlled or sustained rate. The particle may have a diameter between about 1 nm and about 100 microns, or between about 1 nm and 10 microns, 1 nm and 1 micron, 1 and 100 nm, 1 and 50 nm, 50 nm and 10 microns, 100 nm and 10 microns, 500 nm and 10 microns, 1 and 10 microns, 5 and 10 microns, 50 and 50 nm, 100 nm and 1 micron, 100 and 500 nm, 10 and 100 microns, 1 and 100 microns, 10 and 50 microns, 50 and 100 microns or 500 nm and 1 micron, and may have a diameter about 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800 or 900 nm or about 1, 1.5, 2, 2.5, 3, 3.5, 4, 4.5, 5, 6, 7, 8, 9, 10, 15, 20, 25, 30, 35, 40, 45, 50, 60, 70, 80, 90 or 100 microns, or may be more than about 100 microns. Usually the particles are all ≥100 nm except when the particles are produced using mixed alkoxide/ormosil precursors where the particles may be <100 nm (e.g. particles from 50/50 mixed alkoxide/ormosil precursors, which in the case of TEOS/PTMS appear very small (~25 nm). Thus the invention also provides a plurality of particles made using mixed alkoxide/ormosil precursors containing dopant as described earlier, and the mean particle size of the particles may be between about 1 nm and 200 nm.

The particle may be spherical, oblate spherical or may be ovoid or ellipsoid. It may be regular or irregular shaped. It may be non-porous, or may be mesoporous or microporous. It may have a specific surface area of between about 2 and 50 m²/g, or between about 2 and 25, 2 and 20, 2 and 15, 2 and 10, 10 and 50, 10 and 25, 15 and 25 or 20 and 50 m²/g, and may have a specific surface area of about 2, 3, 4, 5, 6, 7, 8, 9, 10, 11, 12, 13, 14, 15, 16, 17, 18, 19, 20, 21, 22, 23, 24, 25, 26, 28, 30, 35, 40, 45 or 50 m²/g. The particle may comprise macropores, and may be macroporous. The macropores may be between about 10 and about 500 nm diameter, or between about 10 and 250, 10 and 100, and 50, 50 and 500, 100 and 500, 250 and 500, 50 and 200 or 50 and 100 mm, e.g. about 50, 100, 150, 200, 250, 300, 350, 400, 450 or 500 nm in diameter.

The particle or particles may be capable of releasing the dopant, e.g. hydrophobic material, over a period of between about 1 minute and 1 month or more, or over between about 1 minute and 1 week, 1 minute and 1 day, 1 minute and 12 hours, 1 minute and 1 hour, 1 and 30 minutes, 1 and 10 minutes, 1 hour and 1 month, 1 day and one month, 1 week and one month, 2 weeks and one month, 1 hour and 1 week, 1 hour and 1 day, 1 and 12 hours or 12 and 24 hours, and may be capable of releasing the dopant, e.g. hydrophobic material, over a period of about 1, 2, 3, 4, 5, 6, 7, 8, 9, 10, 15, 20, 25, 30, 40 or 50 minutes, 1, 2, 3, 4, 5, 6, 9, 12, 15, 18 or 21 hours, 1, 2, 3, 4, 5 or 6 days, 1, 2, 3 or 4 weeks or 1 month or more than one month. The period of time for the particles per se or the particles made by the process of the invention may be in the range from 5 minutes to 72 hours or more, 10 minutes to 72 hours or more, 15 minutes to 72 hours or more, 20 minutes to 72 hours or more, 25 minutes to 72 hours or more, 30 minutes to 72 hours or more, 60 minutes to 72 hours or more, 90 minutes to 72 hours or more, 120 minutes to 72 hours or more, 5 minutes to 48 hours, 10 minutes to 48 hours, 15 minutes to 48 hours, 20 minutes to 48 hours, 25 minutes to 48 hours, 30 minutes to 48 hours, 60 minutes to 48 hours, 90 minutes to 48 hours, 120 minutes to 48 hours, 5 minutes to 24 hours, 10 minutes to 24 hours, 15 minutes to 24 hours, 20 minutes to 24 hours, 25 minutes to 24 hours, 30 minutes to 24 hours, 60 minutes to 24 hours, 90 minutes to 24 hours, 120 minutes to 24 hours, 5 minutes to 12 hours, 10 minutes to 12 hours, 15 minutes to 12 hours, 20 minutes to 12 hours, 25 minutes to 12 hours, 30 minutes to 12 hours, 60 minutes to 12 hours, 90 minutes to 12 hours, 120 minutes to 12 hours, 5 minutes to 6 hours, 10 minutes to 6 hours, 15 minutes to 6 hours, 20 minutes to 6 hours, 25 minutes to 6 hours, 30 minutes to 6 hours, 60 minutes to 6 hours, 90 minutes to 6 hours, 120 minutes to 6 hours, 5 minutes to 3 hours, 10 minutes to 3 hours, 15 minutes to 3 hours, 20 minutes to 3 hours, 25 minutes to 3 hours, 30 minutes to 3 hours, 60 minutes to 3 hours, 90 minutes to 3 hours, 120 minutes to 3 hours, 5 minutes to 2 hours, 10 minutes to 2 hours, 15 minutes to 2 hours, 20 minutes to 2 hours, 25 minutes to 2 hours, 30 minutes to 2 hours, 60 minutes to 2 hours, 90 minutes to 2 hours, or 5 minutes to 1 hour. The rate of release of the dopant, e.g. hydrophobic material, may be characterised by a half-release time, which is the time after which half of the original amount of hydrophobic material has been released. The particle(s) may have a half-release time of between about 1 minute and 1 month or more, as described above. The particle (s) may therefore be used in applications requiring sustained release over relatively short periods, for example between about 1 minute and about 1 hour, or they may be used in applications requiring sustained release over intermediate periods, for example between about 1 hour and about 1 day, or they may be used in applications requiring sustained release over relatively long periods, e.g. greater than 1 day (e.g. between about 1 day and 1 year). The particles may be in the form of a composition together with an acceptable carrier, diluent, excipient and/or adjuvant. Where the dopant is a pharmaceutical substance the carrier may be a pharmaceutically acceptable carrier and the particles may be pharmaceutically acceptable, where the dopant is a veterinary substance the carrier may be a veterinarilly acceptable carrier and the particles may be veterinarilly acceptable, where the dopant is a biocidal substance the carrier may be a biocidally acceptable carrier and the particles may be biocidally acceptable, where the dopant is a pesticidal substance the carrier may be a pesticidally acceptable carrier and the particles may be pesticidally acceptable, where the dopant is a cosmetic substance the carrier may be a cosmetically acceptable carrier and the particles may be cosmetically acceptable, where the dopant is a herbicide substance the carrier may be a herbicidally acceptable carrier and the particles may be herbicidally acceptable, where the dopant is a agaricide substance the carrier may be a agaricidally acceptable carrier and the particles may be agaridally acceptable, and where the dopant is a fungicidal substance the carrier may be a fungicidally acceptable carrier and the particles may be fungicidally acceptable.

The features described throughout the specification or claims for the particles of the invention may be present in the particles in any workable combination of features.

The particles of the present invention may be used for treating a condition in a subject by administering to the subject a therapeutically effective quantity of the particles, or a composition containing the particles, wherein the dopant, e.g. hydrophobic material, of the particles is releasable from said particles and is indicated for the condition. The subject may be a vertebrate, and the vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, cow, bull, ox, buffalo, sheep, dog, cat, goat, llama, rabbit, ape, monkey and a camel, for example. The dopant, e.g. hydrophobic material may be a drug, and the drug may be an anti-cancer drug. The condition may be a disease. The condition may be for example cancer, diabetes, hormonal disfunction, hypertension, pain or some other condition. An effective amount of the particles to treat the condition may be administered. The particles may be administered by injection (intravenously or intramuscularly), orally, by inhalation, topically or by any other suitable means. The dopant, e.g. hydrophobic material, may be an oil, a nutraceutical, a vitamin supplement or a dietary supplement, for example an omega-3 unsaturated oil.

The particles of the present invention may be used for delivering a dopant, e.g. hydrophobic material. This may comprise exposing the particles according to the present invention to a medium capable of releasing the dopant, e.g. hydrophobic material, therein. The dopant, e.g. hydrophobic material, should be releasable from the particles. The exposing may comprise immersing the particles in the medium, and may additionally comprise one or more of stirring, shaking, swirling or otherwise agitating the medium having the particles therein. The medium should be capable of releasing or extracting the dopant, e.g. hydrophobic material, from the particles, and may be capable of dissolving the dopant, e.g. hydrophobic material. The releasing or extracting may be over an extended period of time, as described earlier.

Alternatively the exposing may comprise passing the medium past and/or through the particles. The medium may be a fluid, and may be a liquid. The medium may be a biological fluid such as blood. It may be an organic fluid, and may be an organic solvent, for example a hydrophobic solvent. It may be for example water, methanol, ethanol, propanol, isopropanol, a liquid hydrocarbon (e.g. pentane, hexane, heptane, octane, decane, cyclohexane, benzene, toluene, xylene), a chlorinated solvent (e.g. chlorobenzene, dichlorobenzene, chloroform, dichloromethane, carbon tetrachloride, ethylene dichloride, dichloroethane, methyl chloroform), an ester (e.g. ethyl acetate), an ether (e.g. diethyl ether) or some other hydrophobic liquid. The medium may be capable of dissolving or releasing the dopant, e.g. hydrophobic material. The dopant, e.g. hydrophobic material may be for example a fluorescent dye, a radiopharmaceutical, a drug, an enzyme, a hormone, a biocide, a flavour, an aroma substance, an oil, a nutraceutical, a vitamin supplement or some other substance, or it may be a mixture of any two or more of these. The medium may be a gas, for example air, nitrogen, oxygen, helium, argon, carbon dioxide, or a mixture of gases, and the dopant, e.g. hydrophobic material, may be volatile (for example an aroma material). The exposing may be under conditions suitable for release of the dopant, e.g. hydrophobic material, into the medium, for example conditions of temperature, pressure, ratio of particles to the medium etc.

The features described throughout the specification or claims for the method of the invention may be present in any workable combination of method steps.

Possible benefits of the present invention include:
the continuous phase used in making the particles of the invention may be aqueous, thereby reducing cost and facilitating waste disposal, and reducing problems of residual continuous phase on or in the particles;
the surfactant used in the process may be removed by washing with water;
the process is capable of achieving good incorporation efficiencies;
the size of the particles may be tailored to meet the requirements of different applications;
the possibility to achieve high loading of dopant within the particles;
the possibility to extend the range from nanoparticles to submicron and micro-particles;
the possibility to release the dopant (e.g, hydrophobic material) in a controlled fashion;
it is not essential to use a solvent to dissolve the dopant (e.g., hydrophobic material), which may have particular advantages with respect to drug delivery etc., as organic solvents may be toxic and/or difficult to eliminate;
protection of the dopant (e.g, hydrophobic material) from the external environment, whereby for example, unwanted reactions or decomposition is avoided, e.g, oxidation of retinol.

The main difference between the particles produced by the present invention and A. Maitra et al is that the particles produced by A. Maitra et al. are hollow, consisting of a silica shell which is formed as OTES reacts at the micellar interface. In contrast, the particles of the present invention consist of solid matrices containing vacuoles which may be macroporous. Also particles of the present invention contain amine groups, which enhances the hydrophilicity and improves suspension in protic solvents (particularly water). The possibility to encapsulate a hydrophobic compound in an hydrophilic matrix is a major step towards solving the problem of the delivery of poorly soluble drugs orally by increasing both there solubility in biological media as well as their permeability through the gut wall.

In relation to Prasad et al. the particles of the present invention may be produced rapidly in an unstable emulsion, which results in particles with a wider size distribution but a tunable average size. Conversely, the particles prepared according to Prasad et al. are grown slowly in micelles, giving monodispersed particles or particles with a narrow size distribution but a size fixed around 30 nm in diameter. Prasad et al. state that their particles do not significantly release hydrophobes. In contrast, the particles of the present invention, however, do comprise dopant which is releasable from the particles. The extent of release depends on the hydrophobe and the loading, but the present inventors have observed release of 80 wt % of the encapsulated hydrophobe. The difference is probably due to the difference in particle size and internal structure (i.e. porosity), which also impacts on the loading achieved. Cross-section TEM of a 12 micron particle of the present invention shows a number of vacuoles, with an average size of 230 nm. These large voids are linked to the high loading of active in the particles, and enables greater release of the dopants. Regarding the composition of the particles of the present invention, they may have 5-25 mol % aminopropylsiloxane (when aminopropyltrialkoxysilane is used as a catalyst to make the particles) incorporated in the particles. This is likely to be considerably higher than the amount incorporated in the Prasad et al. particles, as they use 20 times less APTES as a catalyst. The amount of aminopropyl siloxane incorporated in the particles is expected to have a significant effect on the matrix microstructure. It is well known that the nature of the organic substituent group of the organically modified siloxane has a strong influence on the degree of condensation of organically modified silica networks and thus on the microstructure of the particle. Moreover, because of the catalytic activity of the aminopropyl siloxane on the condensation of the partially hydrolized silica precursor, one could expect a strong variation of the internal microstructure of the particle with the amount of catalyst used. This could explain another surprising feature of the particles of the present invention, that their surface area appears to be close to their geometric surface. In other words, the particles appear non-porous (i.e. no porosity detected by nitrogen adsorption). This is different from the disclosures of both Prasad et al. and A. Maitra et al. who describe their is particles as having mesoporosity and advance the figure of 5 nm for average pore size (no measurement). The fact that the particles of the present invention can release 80% of their content in ethanol, suggests that there is some porosity through which the active can diffuse. Moreover, this apparent contradiction between release behaviour and porosity measurement suggests that the release mechanism could occur by swelling of the matrix under appropriate conditions or with time. The swellability of the organically modified framework is linked to the flexibility of the silica framework and thus its degree of condensation (or crosslinking) and thus to the initial catalyst/precursor ratio. In other words, the particle internal microstructure is unique to the process and initial precursor mix. Finally the loading of dopant inside the particles prepared by the present invention may be also more than one order of magnitude higher than the particles produced by Prasad et al. (~10 wt % for the particles of the present invention vs ~0.3 wt % for the particles of Prasad). It may be that these high loadings can only be achieved using the process of the present invention, which involves the production of larger particles in an unstable emulsion rather than very small nanoparticles via micelle synthesis. For any industrial controlled release applications it is critical to achieve significant loadings ≥5 wt %. One other feature of the particles is that they do not contain residual organic solvent such as DMF or DMSO used to dissolve the hydrophobic active (e.g. Prasad et al.) which are highly toxic substances and very difficult to eliminate once incorporated inside the particles.

The process of the present invention is based on the use of "true emulsions" which are relatively unstable compared to micro-emulsions (stabilised with a co-surfactant) or micellar solution. It is the relative unstability of the system of the present invention that allows the rapid, high yield, production of micron size particles as well as the high loading of actives. In an experiment the present inventors have shown that, in the system of the present invention, the droplet size increases significantly (from 18 nm to 380 nm for one precursor (vinyltrimethoxysilane), and from 18 to 950 nm for an alternative precursor (ethyltrimethoxysilane)) after the addition of an APTES catalyst. Conversely, the droplet size slowly increases with time for the process disclosed by Prasad et al. This suggests two different growth mechanisms for the two different processes. In the case of Prasad et al, the micelles act as rigid nano-reactors in which the condensation of the ormosil take place, catalysed by the amino group from APTES or ammonia interacting at the surface of the micelles. In contrast, in the process according to the present invention, formation of the particles takes place by coalescence of the emulsion droplets induced by the addition of APTES. The fact that the process of the present invention does not produce particles with ammonia (in contrast to what has been reported in US2004/0180096) suggests the necessity for the catalyst to penetrate the emulsion walls and its participation in the condensation reaction. The fact that in an exemplified process of the present invention significantly more aminopropylsiloxane is incorporated in the particles (despite having much larger particles and thus a much smaller geometric surface area) further confirms that aminopropylsiloxane is incorporated inside the organo-silica matrix and is not solely dispersed at the surface of the particles.

From an industrial perspective, the process of the present invention allows the production of particles with high loading (10 vs 0.3%), at a high yield (dependent on the amino/ormosil ratio), instantaneously (vs 24 h). In addition the process of the present invention does not require the addition of toxic solvent such as DMF or DMSO to dissolve the hydrophobic payload. It can be dissolved directly inside the surfactant or the silicon precursor.

Throughout the specification and claims the terms hydrophobic material, hydrophobe(s), hydrophobic active(s), hydrophobic active molecule(s) and hydrophobic active material(s) may be used interchangeably.

Embodiments of the invention will now be described with reference to the following non-limiting examples.

EXAMPLES

Synthesis

Methodology

Figure 3:
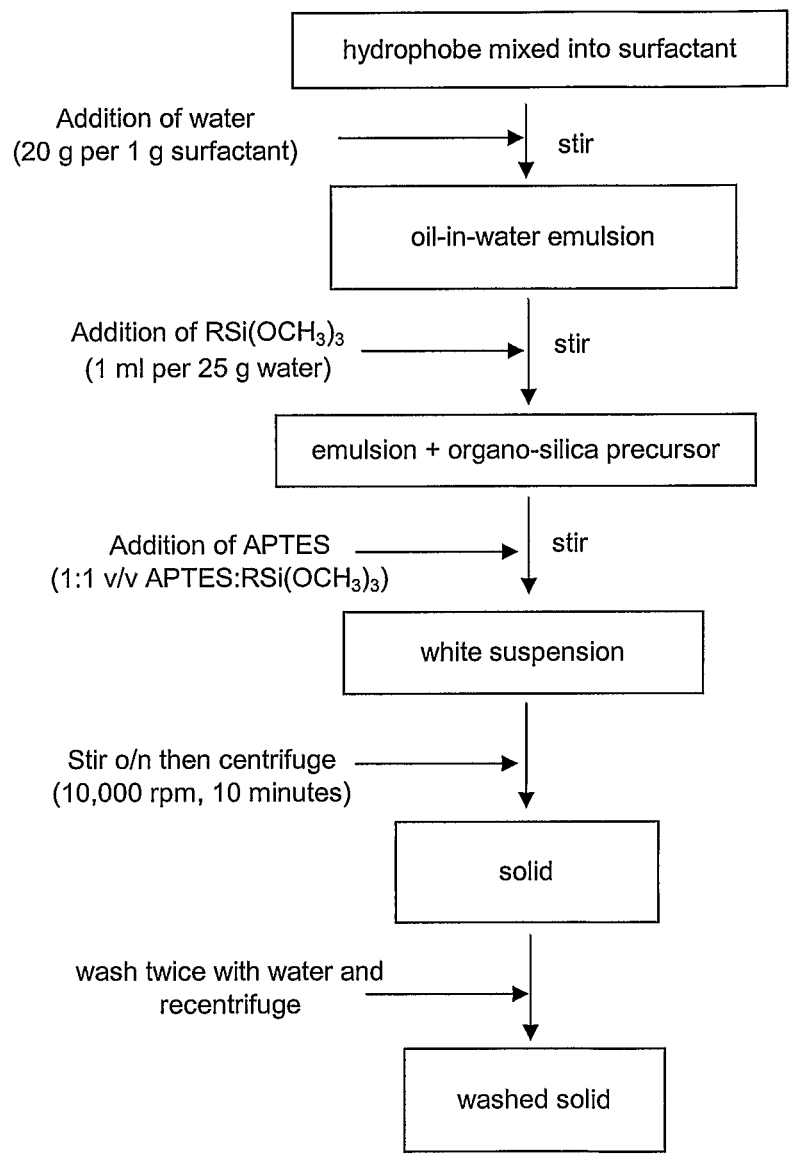
FIG. 3 is a flow chart of a procedure for producing organosilica particles according to the present invention.

The basic synthetic method is described by the flow diagram in FIG. 3. Typically, a hydrophobe was dissolved in surfactant, followed by addition of water (in a 1:20 weight ratio of surfactant:water) to form an emulsion. An ormosil with volume ratio 1:25 (ormosil:water) was added to the emulsion, and then APTES (aminopropyltriethoxysilane) was added in the same volume amount as the ormosil. This formed a white emulsion, which was stirred overnight. The resulting solid particles were separated by centrifuging at 10,000 rpm for 10 minutes and the supernatant was decanted. The solid was washed twice, by resuspending the particles in water and centrifuging.

Surfactant

The surfactant typically used was NP-9 (HLB=12.8), which is a nonylphenoxypolyethoxyethanol, $C_9H_{19}C_6H_4(OCH_2CH_2)_nOH$ with average n=9. Other closely related surfactants which were used are Triton X-100 (HLB=13.5) and Triton X-114 (HLB=12.4), which are $C_8H_{17}C_6H_4(OCH_2CH_2)_nOH$, average n=9 and 8, respectively. Other surfactants which were tested, included Tween 20 (HLB 16.7), Tween 80 (HLB 15.0), Brij 35 (HLB 16.9), and SDS (anionic surfactant). Important factors are considered to be the HLB and the pH of the resulting solution, as the ormosil is known to be at least partially hydrolysed before addition of APTES, as observed by IR. A solution of NP-9 in water (1:20 w/w) results in a pH of ~4.5, where that of Triton X-100 is 4.3, and Triton X-114 is 5.8. However, the Tween solutions give a similar pH, so pH alone is not a sufficient condition for achieving particles.

The surfactant concentration most commonly used is 1:20 (w/w) surfactant:water. Concentrations of 1:10 (w/w) have also been used; the increased concentration doesn't appear to have a significant effect on the particles produced.

Hydrophobe

A number of hydrophobic molecules were encapsulated using the present method: solvent blue 35 and sudan red (organic dyes), limonene (liquid) and diuron and retinol (solids). Encapsulation efficiencies for solvent blue and retinol were approximately 50% (i.e. 50% of the dopant supplied was encapsulated in the resulting solid), based on analysis of the supernatant solutions by UV/VIS spectroscopy. Determination of the concentration in the supernatant enables an estimation of the concentration inside the particles. However, encapsulation efficiencies for limonene are more difficult to determine, as the analysis must be done by HPLC, and the supernatant solutions are too highly concentrated in surfactant thus perturbing the HPLC measurement (interference of the surfactant peak with the limonene peak). Leach solutions in which the particles have been suspended for several days in ethanol have been analysed. It is possible, however, that not all the encapsulated limonene has been released after this time. Thus, while the release of limonene suggests encapsulation efficiencies in the range 15-20%, the real value might be higher than this. Samples with relatively high loadings of limonene in the reaction mixture (15 ml limonene: 30 ml PTMS) were found to be soluble in acetone and partially soluble in chloroform. HPLC analysis showed that a weight equivalent to about 3% was removed from the solid on leaching in ethanol, whereas IR analysis of a chloroform solution in which the particles are partially soluble, suggested a weight loading of 5%.

Ormosil

A selection of ormosils was tested using this synthetic method, as well as the unmodified alkoxide tetraethylorthosilicate (TEOS). Initial trials involved doping with solvent blue dyed limonene, so that the particle colour indicated whether the hydrophobic molecule had been encapsulated. Of the ormosils tried, vinyltrimethoxysilane (VTMS), phenyltrimethoxysilane (PTMS), and ethyltrimethoxysilane (ETMS) resulted in blue particle formation. TEOS, hexadecyltrimethoxysilane and methyltrimethoxysilane gave colourless particles, indicating that the hydrophobic dye had not been encapsulated for these precursors, or was easily removed during the washing process. No particles were obtained from octyltriethoxysilane. Particles were obtained from phenyltriethoxysilane, but the encapsulation efficiency for the solvent blue 35 dye was lower compared with phenyltrimethoxysilane, so in subsequent work the methoxy precursor was used in preference to the ethoxy for the phenyl-ormosil.

The ormosil is typically added in a ratio of 1:25 (v/v) ormosil:water. However, more concentrated emulsions have been prepared using a ratio of 2:25 (v/v) ormosil:water which results in larger particles, and a broader size distribution.

Although reaction of the silicon alkoxides, tetramethylorthosilicate (TMOS) and tetraethylorthosilicate (TEOS), under the standard preparation conditions, did not result in the production of spherical particles, particles were obtained from precursor mixtures containing 50% TEOS or TMOS and 50% VTMS or PTMS. Particles were not obtained for similar mixtures involving ETMS. Likewise, 75/25% mixtures of alkoxide and alkyltrimethoxysilane did not result in particle formation.

Reaction Mechanism

Figure 4:
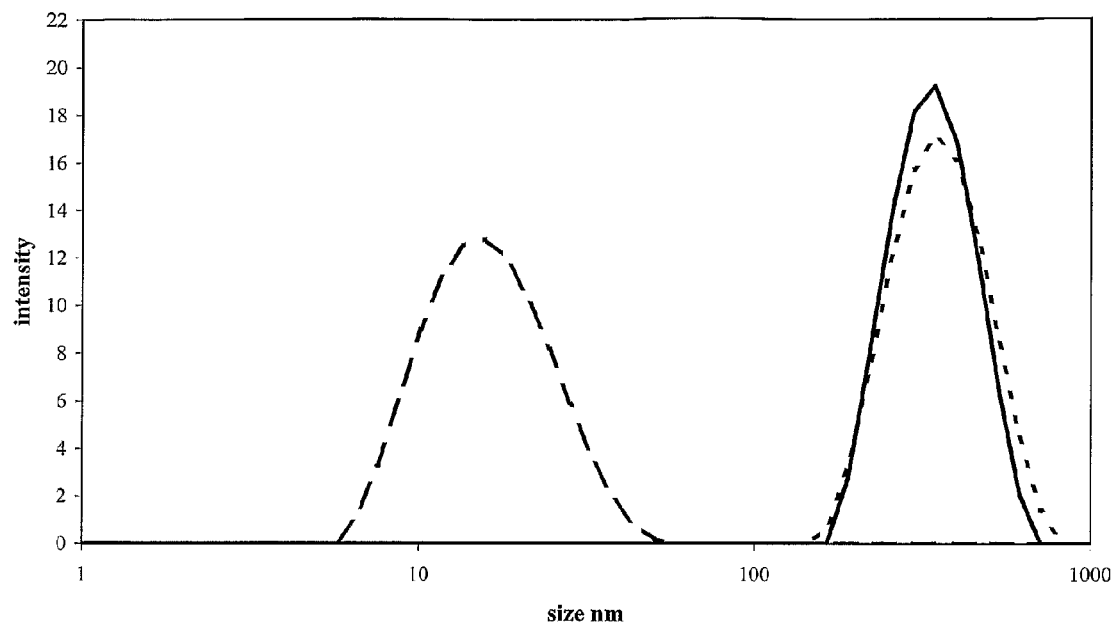
FIG. 4 shows the droplet size for (---) VTMS emulsion before addition of APTES, (---) VTMS emulsion several minutes after addition of APTES, and (-) VTMS emulsion four hours after addition of APTES.

Addition of APTES results in almost immediate destabilisation of the emulsion, causing coalescence of the droplets as observed by photon correlation spectroscopy (PCS). Visually, after an induction period of several seconds, the emulsion turned a milky white colour indicating formation of considerably larger droplets. FIG. 4 illustrates the droplet growth in the case of the VTMS reaction, The droplet size in the VTMS/NP-9/water emulsion is 18 nm. Several minutes after addition of APTES, the droplet size was found to be 380 nm. After four hours, when particles are expected to have been formed, the same droplet size was measured (see FIG. 4).

Addition of APTES catalyses the condensation of organosilica particles, although the amount of product obtained from the reaction of ETMS (see Table 1) suggests that a significant quantity of 3-aminopropylsiloxane was also incorporated into this material. Indeed, N—H stretching bands were observed in IR for all three products, indicating amine incorporation. Earlier work indicated less than 10 mol % incorporation of the amine species in the organosilica from VTMS, and those investigators postulated that the amines were located at the surface of the nanoparticle.

IR analysis showed that the VTMS precursor was largely hydrolysed before addition of the ATPES, whereas PTMS and ETMS are only partially hydrolysed when APTES is added. However, when the addition of APTES was delayed in the case of ETMS, particles were not obtained. The reason for this may be that the hydrolysis product of ETMS ($CH_3CH_2$—$Si(OH)_3$) is soluble in water, and thus the organosilica precursor was not constrained to the hydrophobic phase when condensation occurred. In contrast, the addition time was found not to be critical for PTMS, indicating that the presence of the phenyl ring is sufficient to keep the organosilica precursor inside the hydrophobic phase during the hydrolysis/condensation processes.

As it is likely that the amine group of APTES is responsible for catalysing the formation of Si—O—Si bonds in the organosilica, a number of alternative bases were tested. Sufficient base was added to increase the solution pH to 10, to match the conditions occurring on addition of APTES. The solutions turned white on addition of the bases, suggesting that condensation was catalysed. However, no solid particles were obtained on reaction of VTMS with NaOH and $NH_4OH$, and only very small quantities of solid were retrieved from reactions of VTMS and PTMS with tetrabutylammonium hydroxide and hexylamine. It is possible that APTES is more effective in catalysing the condensation because it is able to penetrate more effectively into the hydrophobic domain.

Alternative aminoalkyl trialkoxysilanes were also trialled as catalysts. 3-Aminopropyltrimethoxysilane, 3-(2-aminoethylamino)propyltrimethoxysilane, and 3-[2-(2-aminoethylamino)ethylamino]propyltrimethoxysilane all resulted in the production of particles, although in each case, the sample appeared more agglomerated than when APTES was used.

APTES was typically added at a 1:1 v/v APTES:ormosil ratio. However, experiments where the APTES:PTMS ratio was progressively lowered from 1:1 to 0.1:1 resulted in particles in all cases. However, the amount of solid particles obtained decreased significantly with decreasing volume of APTES added, resulting in the following product weights (APTES:PTMS ratios): 1.30 g (1:1), 0.88 g (0.5:1), 0.36 g (0.25:1) and 0.16 g (0.1:1).

Particle Characterisation

Particle Size

Figure 5:
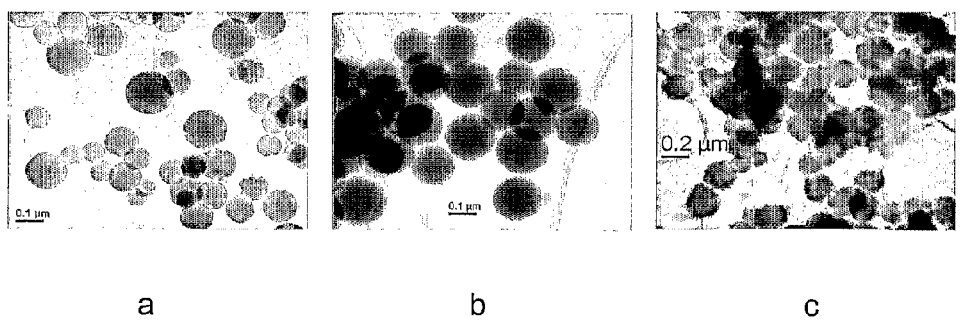
FIG. 5 shows TEM (transmission electron microscope) micrographs of particles synthesized using (1:25 v/v ormosil: water) vinyl-(a), phenyl-(b) and ethyltrimethoxysilane (c)

TEM micrographs of particles produced from VTMS, PTMS and ETMS (1:25 v/v ormosil:water) are shown in FIG. 5. The particles from VTMS ranged from about 50-200 nm, with an average size of about 150 nm. Those from PTMS were of a similar size, with an average size about 170 nm. The particles from ETMS appeared quite different in morphology from both VTMS and PTMS, which had well-defined, smooth surfaces. The ETMS particles appeared more raspberry like, as spherical shaped aggregates about 150 nm. There appeared to be finer material not incorporated into the aggregates which was associated with the particles, although it is not clear at this stage whether this consisted of organosilica or other, perhaps surfactant, material. Doping with relatively low loadings (<10% wt) of limonene did not alter the appearance of the particles.

Figure 6:
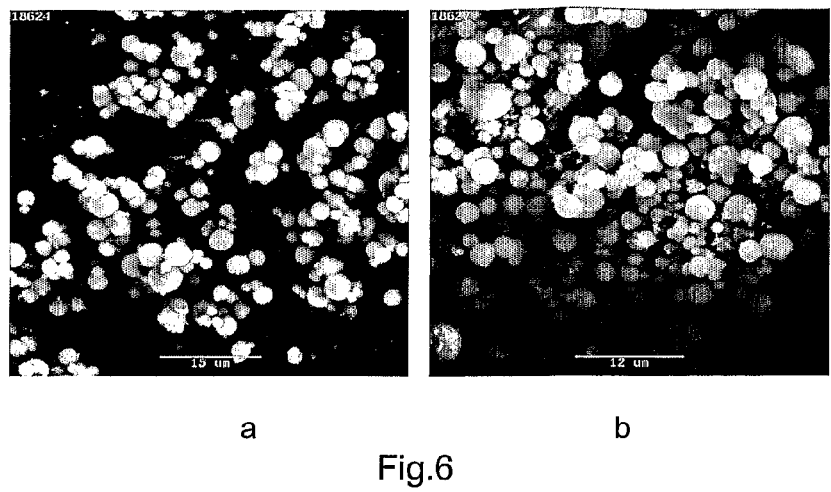
FIG. 6 shows SEM (scanning electron microscope) micrographs of particles formed in concentrated emulsions of VTMS (a) and PTMS (b)

Larger particles (typically up to about 20 μm) in addition to smaller particles were produced in more concentrated emulsions (eg 2:25 (v/v) ormosil:water), as observed in SEM (shown in FIG. 6 for the VTMS and PTMS precursors).

Figure 7:
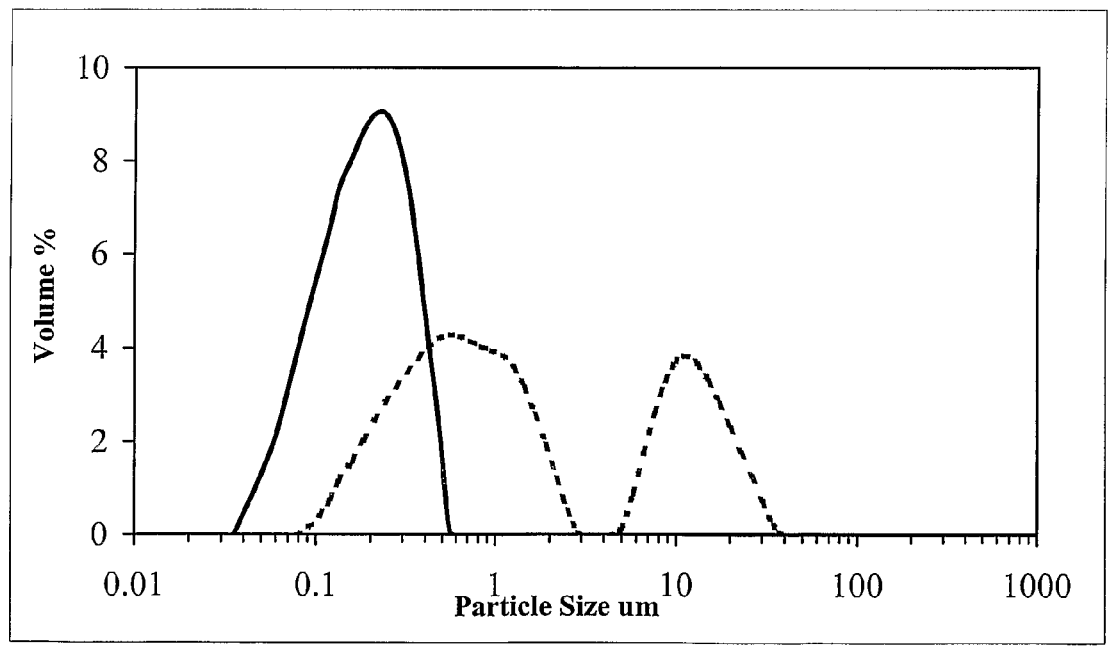
FIG. 7 is a graph showing particle size distribution of vinylsiloxane particles: (-) 1:25 v/v ormosil:water; (--) 2:25 v/v ormosil:water.
Figure 8:
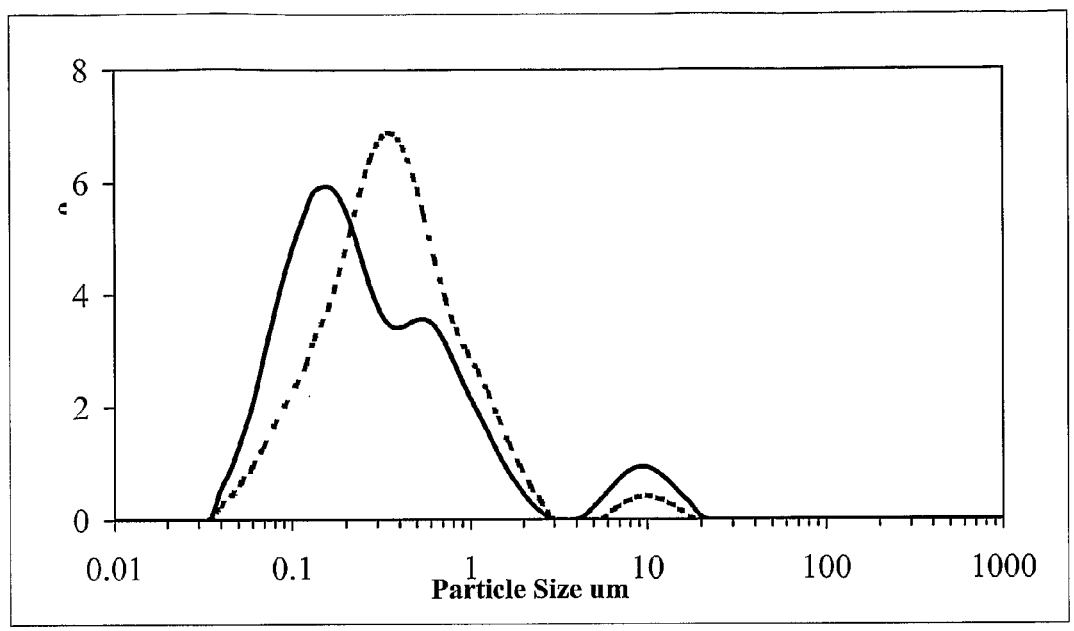
FIG. 8 shows the particle size distribution of phenylsiloxane particles (-) 1:25 v/v ormosil:water, (--), 2:25 v/v ormosil: water.
Figure 9:
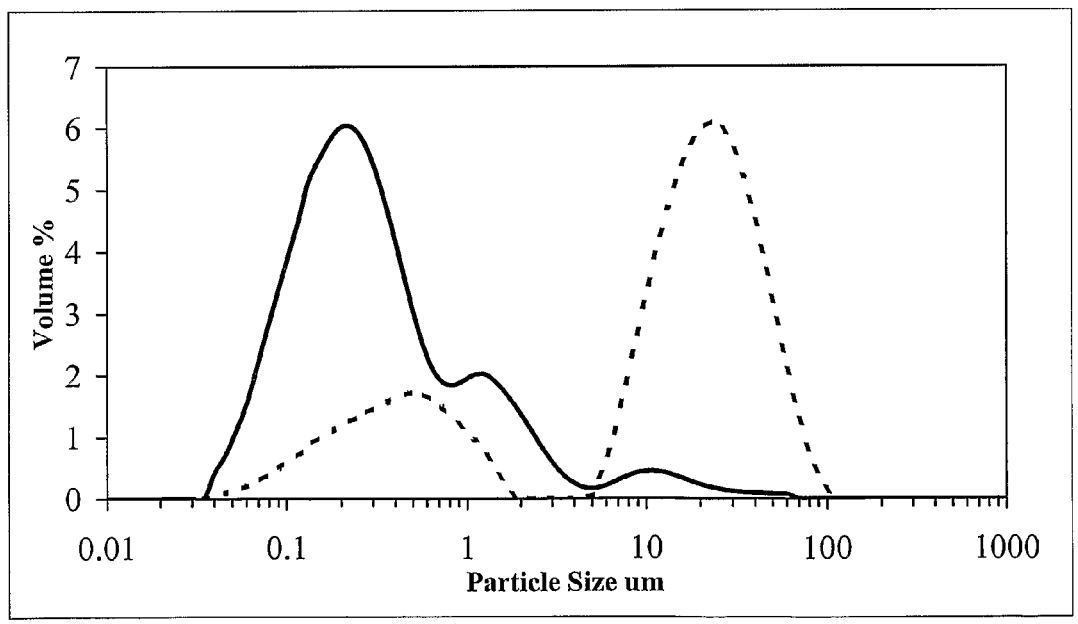
FIG. 9 is a graph showing particle size distribution of ethylsiloxane particles: (-) 1:25 v/v ormosil:water; (--) 2:25 v/v ormosil:water.
Figure 10:
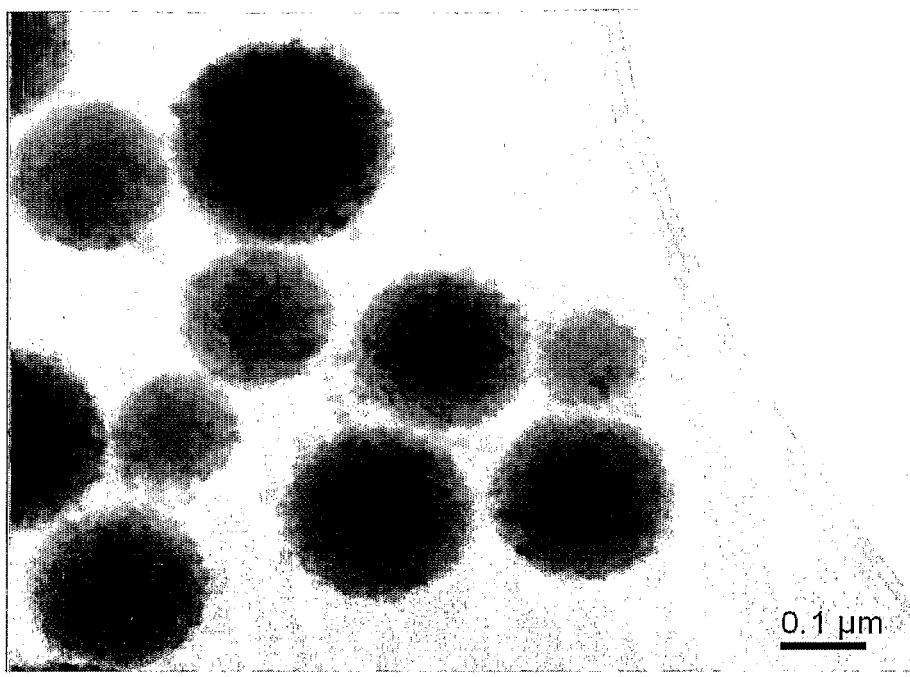
FIG. 10 shows a TEM image of particles obtained from 50/50 (v/v) PTMS/TMOS mixture.
Figure 11:
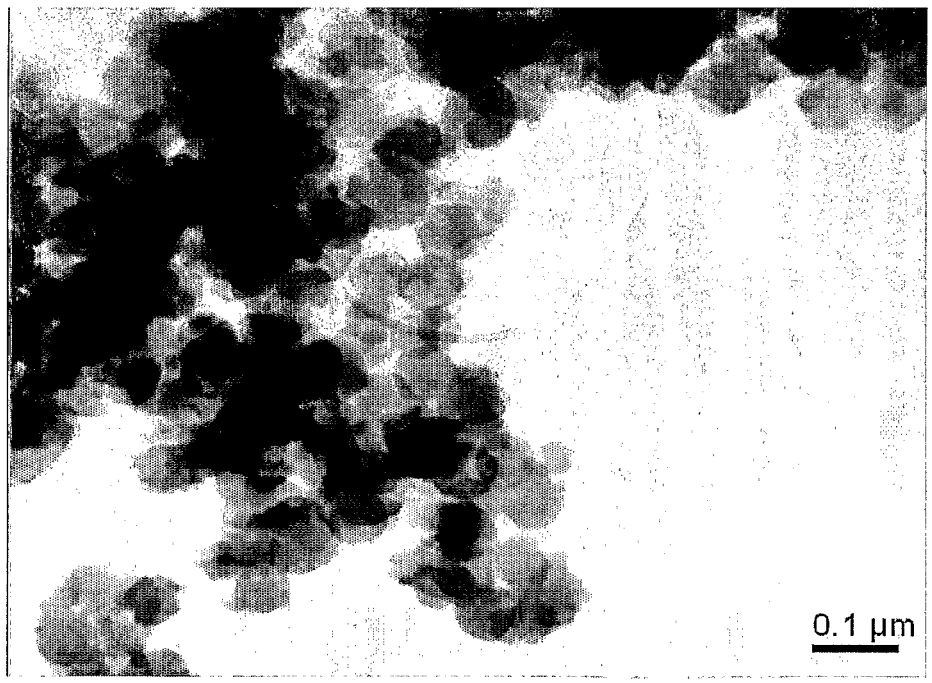
FIG. 11 shows a TEM image of particles obtained from 50/50 (v/v) PTMS/TEOS mixture.
Figure 12:
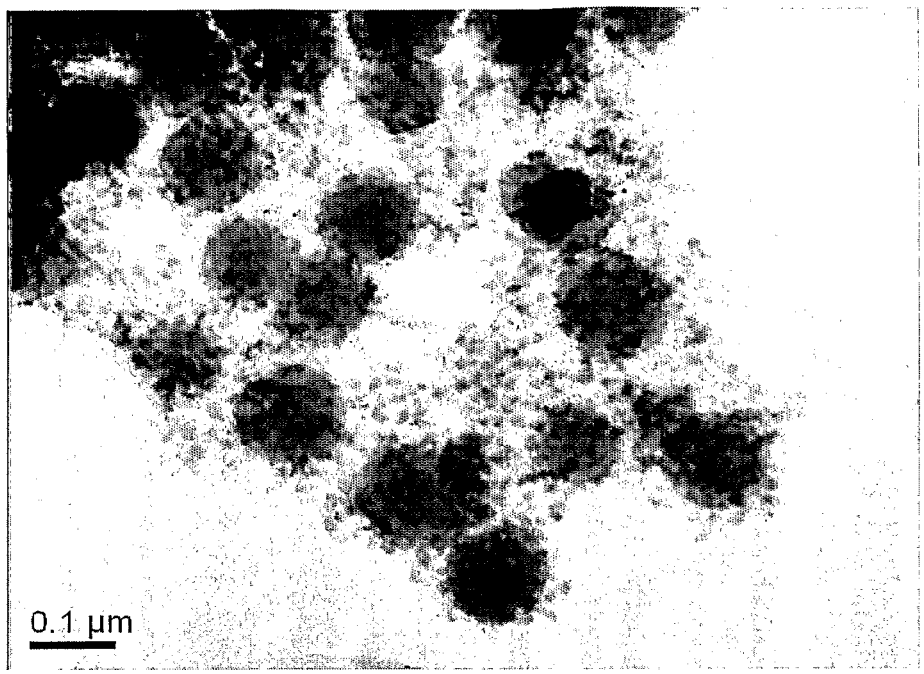
FIG. 12 shows a TEM image of particles obtained from 50/50 (v/v) VTMS/TMOS mixture.
Figure 13:
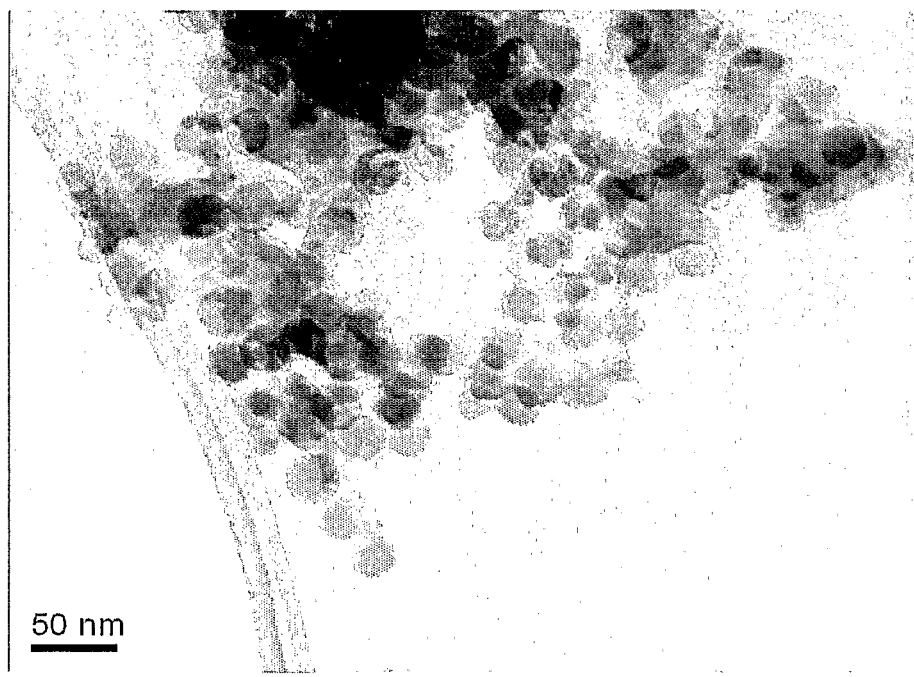
FIG. 13 shows a TEM image of particles formed from 50/50 (v/v) VTMS/TEOS mixture.

Light scattering is capable of providing a more accurate picture of the size distribution of particles for samples in which a range of sizes occurs (i.e. the sample is not monodisperse), compared with TEM. Distributions were measured of samples suspended in water using a Mastersizer 2000, as shown in FIGS. 7-9. While particles under 1 micron in diameter were still obtained when the concentration of reactant was increased (e.g. 2:25 v/v ormosil:water compared with 1:25 v/v ormosil:water), the general trend was for the proportion of larger particles in the sample to increase with increased reactant concentration.

Figure 14:
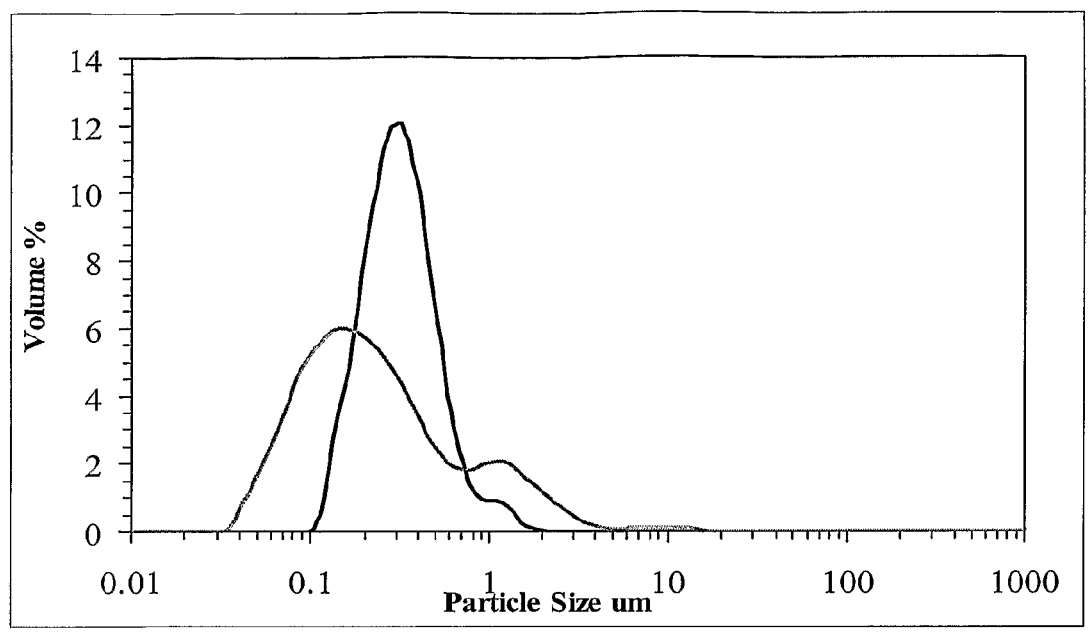
FIG. 14 shows a graph of particle size distribution of particles obtained from (-) 50/50 v/v PTMS/TMOS and (---) 50/50 v/v PTMS/TEOS.
Figure 15:
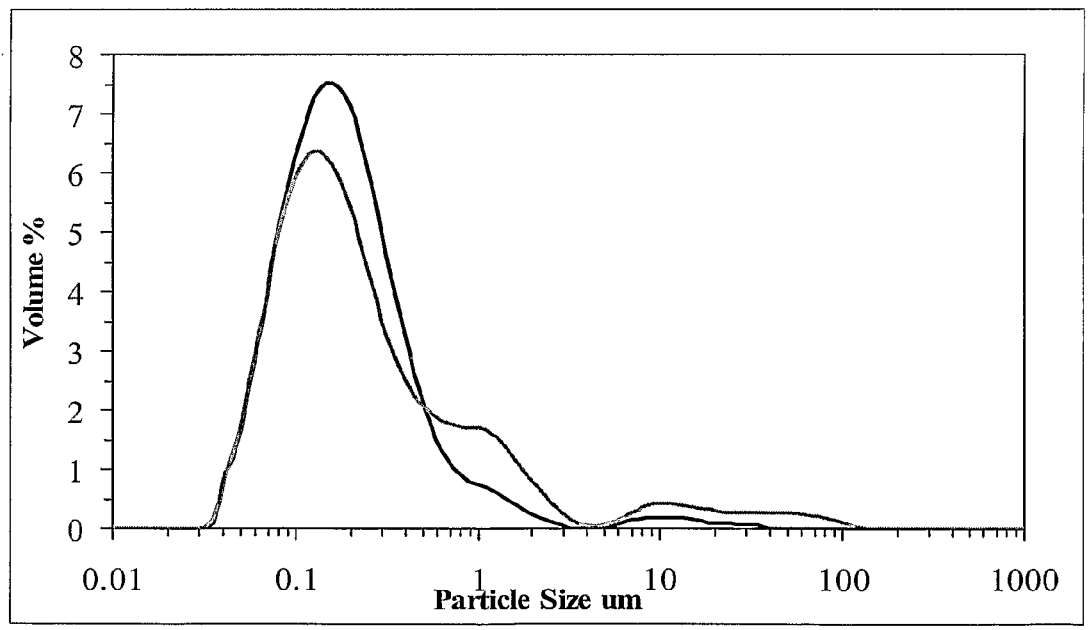
FIG. 15 shows a graph of particle size distribution of particles obtained from (-) 50/50 v/v VTMS/TMOS and (---) 50/50 v/v VTMS/TEOS.

TEM images of products from the 50/50 mixtures (FIGS. 10-13) show that the incorporation of alkoxide into the precursor mix has a substantial effect on the particle size and morphology. Different results are obtained when TMOS is used, compared with when TEOS is used. This may be related to the difference in water solubility between TMOS and TEOS. TEOS is largely insoluble in water, and so is expected to be located preferentially in the hydrophobic droplet alongside the ormosil reactant. However, TMOS is considerably more soluble in water and can easily migrate into the main solvent phase of the emulsion. The particles made using TMOS appear to be bimodal, suggesting that there may be more than one reaction site, where those made using TEOS appear to have a single particle size of about 20-50 nm. The TEOS/ormosil particle size determined by light scattering was somewhat higher (about 100 nm), which may reflect the aggregated nature of these nanoparticles. (See FIGS. 14-15).

Surface Area and Porosity

Figure 16:
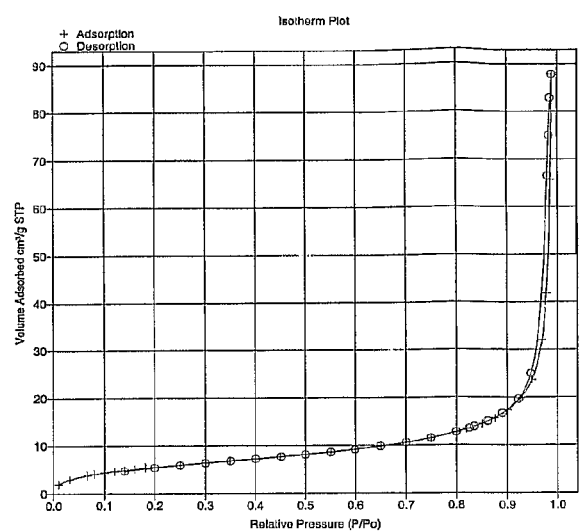
FIG. 16 shows an adsorption/desorption isotherm of organosilica particles produced from VTMS according to the present invention.

The surface area and porosity of dried particles made from the VTMS precursor were determined by $N_2$ sorption using a Micromeritics 2000 ASAP system. The BET surface area was found to be 21.3 $m^2$ $g^{-1}$, consistent with dense, nonporous particles of average size about 200 nm. FIG. 16 shows the adsorption/desorption isotherm indicating that the material does not contain significant measurable micro- or mesoporosity. The volume adsorbed at high partial pressure corresponds to the inter-particle pores. Nevertheless, as release of encapsulated dopants is observed in solution, it is likely that the matrix is porous, but the pores are blocked by the presence of organic groups in the dried material.

Thermal Analysis

Figure 17:
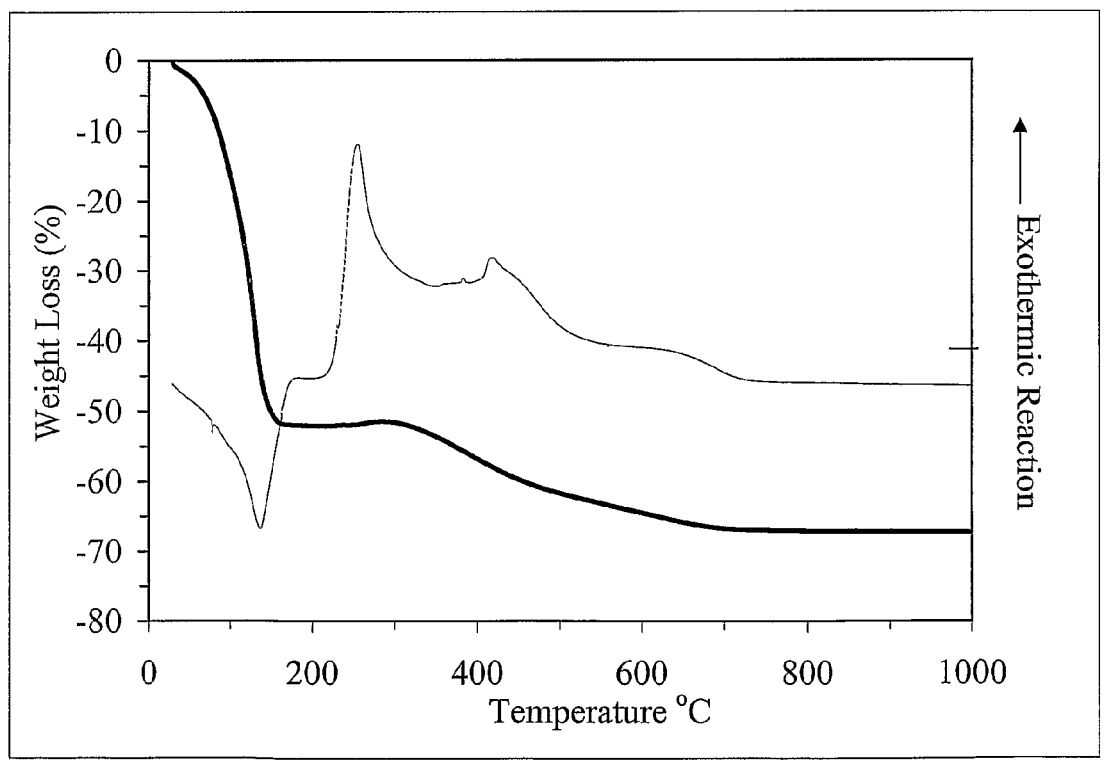
FIG. 17 shows DTA (thin line)/TGA (heavy line) plot of VTMS product according to the present invention.
Figure 18:
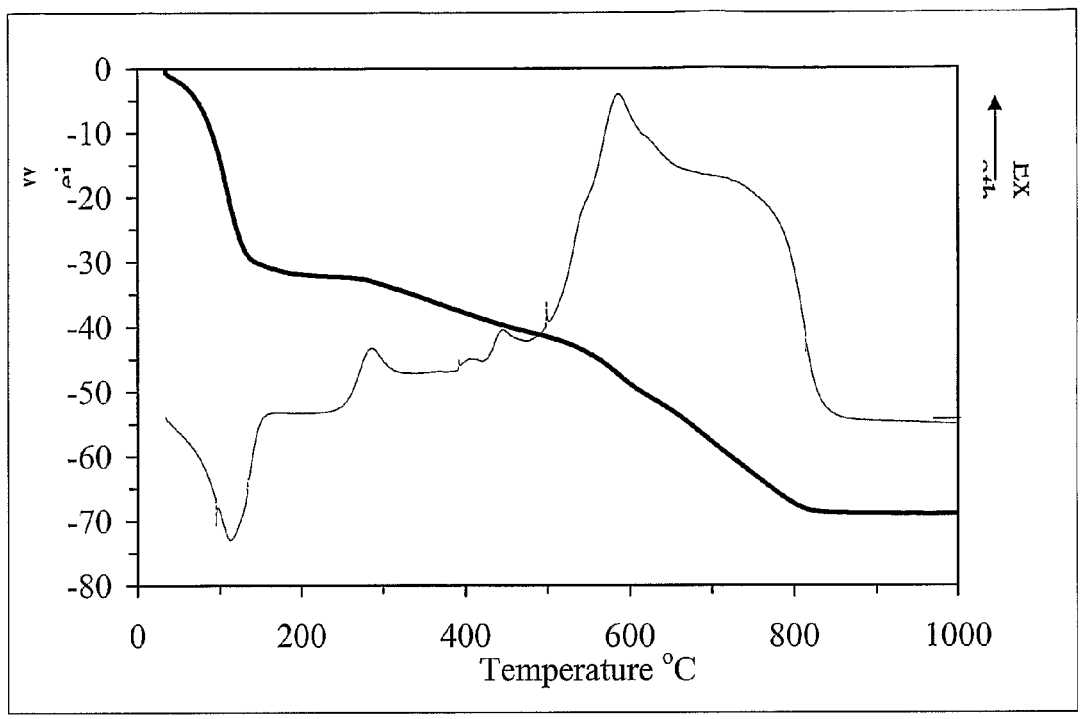
FIG. 18 shows DTA (thin line)/TGA (heavy line) plot of PTMS product according to the present invention.
Figure 19:
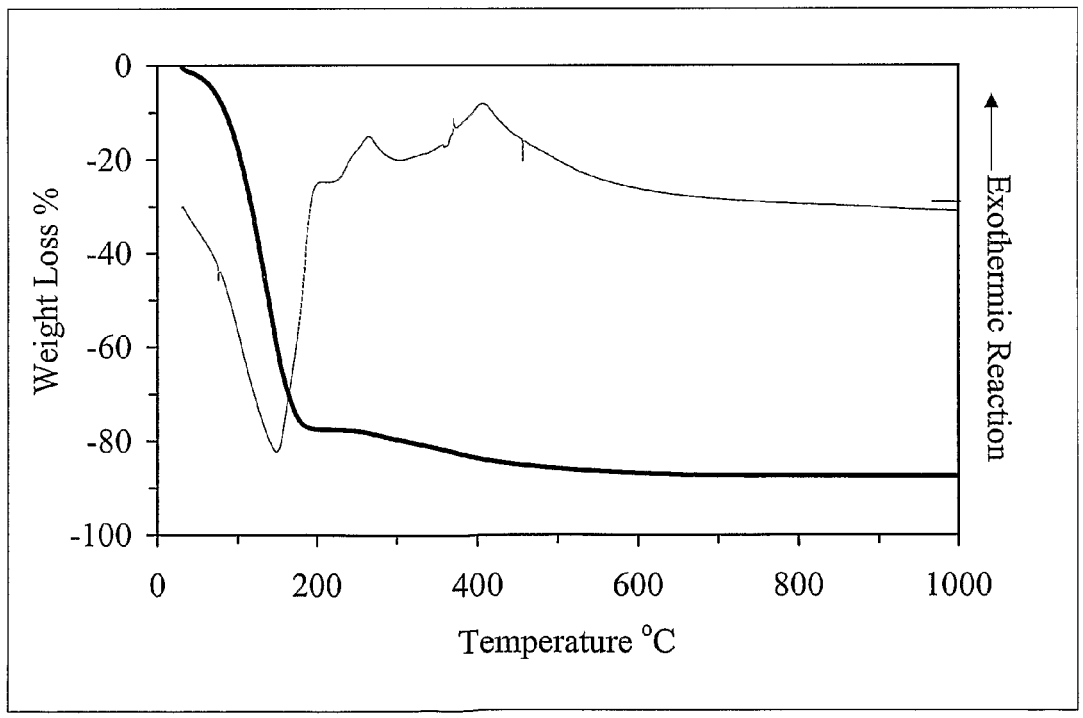
FIG. 19 shows DTA (thin line)/TGA (heavy line) plot of ETMS product according to the present invention.

DTA/TGA analysis was carried out in air using a Setaram thermoanalyser. FIGS. 17, 18, and 19 show the results for the VTMS, PTMS and ETMS products, respectively. The volatiles (water and limonene) were lost by 200° C. The DTA curves suggest that the surfactant loss peaks at 275° C. Comparison of the DTA of PTMS and ETMS products suggests that the amine (present in both samples) and ethyl groups were removed between 400 and 500° C., and phenyl between 600 and 800° C.

The product from VTMS contained 52 wt % volatiles. The VTMS TGA curve is somewhat problematic in that the weight appears to increase slightly around 300° C., after removal of some organics. This effect is most likely due to the very large heat flow measured in this instance, creating buoyancy in the sample. The organic component was 31 wt % of the solid (lost by 700° C.), and the Si—O component, 69 wt %.

The product from PTMS contained 32 wt % volatiles. The composition of the solid is 54% organic (including some adsorbed surfactant), which was finally removed by 800° C. and 46% Si—O.

The product from ETMS contained a very high volatile component (water and limonene) of 78 wt %. The solid consisted of 43 wt % organic (including adsorbed surfactant), finally removed by 600° C., and 57 wt % Si—O. The weight percentage of Si—O relative to the organic fraction appears to be overestimated, possibly due to oxidation occurring when the organic material is driven off at temperature, thereby reducing the final weight loss. Table 1 shows the product yield for 1:1 (v/v) APTES:ormosil reaction, as determined by DTA/TGA for the three products.

TABLE 1

Product yield for given reactant quantities for VTMS, PTMS and ETMS.

|  | APTES (g/equivSi*) | Ormosil (g/equivSi*) | Weight $RSiO_{1.5}$(TGA)** |
|---|---|---|---|
| VTMS | 1 | 1.1 | 1.0 |
| PTMS | 1 | 1.5 | 1.4 |
| ETMS | 1 | 1.1 | 1.8 |

*calculated as weight equivalent of R—$SiO_{1.5}$, where R represents the appropriate organic substituent in each case.
**solid weight (adjusted for volatiles - includes some surfactant).

Infrared Spectroscopy

Figure 20:
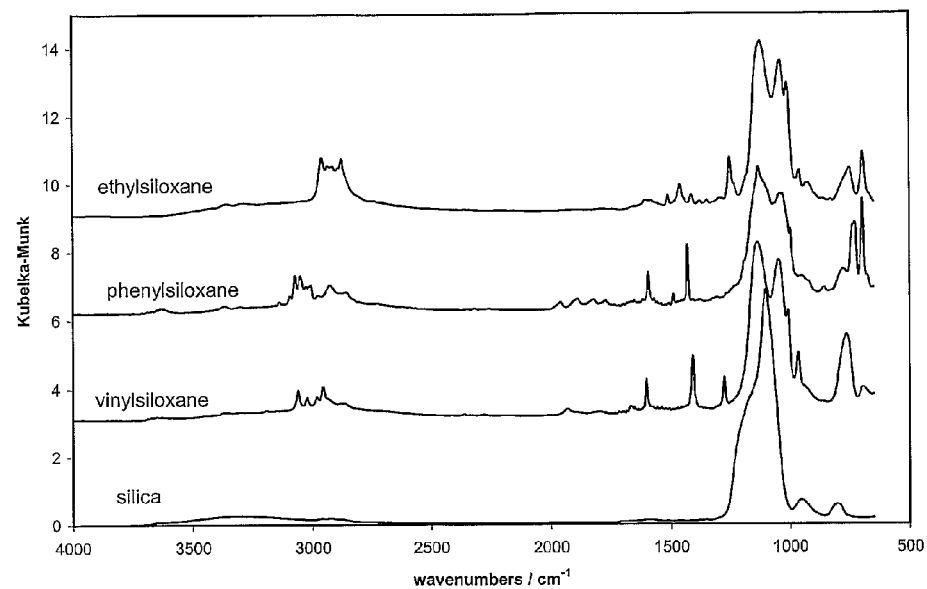
FIG. 20 shows IR diffuse reflectance spectra of organosilica powders according to the present invention (ethylsiloxane, phenylsiloxane and vinylsiloxane) and silica, all diluted to approx. 3 wt % in KBr.

Dried particles were analysed by DRIFT (diffuse reflectance infrared) spectroscopy, and the spectra compared with a spectrum typical of nanoparticulate silica (see FIG. 20). In contrast to $SiO_2$, the organo-silicas should have a composition $RSiO_{1.5}$, where R is a mixture of vinyl (CH=$CH_2$) and aminopropyl ($NH_2(CH_2)_3$) groups in the case of VTMS particles, phenyl ($C_6H_5$) and aminopropyl groups in the case of PTMS particles, and ethyl ($CH_3CH_2$) and aminopropyl groups in the case of ETMS particles. It appears likely that the aminopropyl groups were incorporated into the PTMS and ETMS particles to a greater extent than in the VTMS particles, judging by the typical weight of product obtained (see Table 1).

The most obvious difference between the organo-silica spectra and that of silica, is the change in the main Si—O antisymmetric stretching mode, which in the case of silica consists of an intense absorption at about 1100 $cm^{-1}$ with an asymmetric shoulder to higher energy typical of disordered $SiO_2$. In the organo-silicas this main band is split, due to the presence of the organic substituent. The organo-silica spectra also contain a number of sharp bands below 1600 $cm^{-1}$, which are C—H deformation modes typical of the particular substituent present. There are also C—H stretching modes in the region 3100-2800 $cm^{-1}$ (aryl and alkyl) due to the substituent and residual methoxy/propyl groups. Much weaker alkyl C—H stretching bands in the silica spectrum are due to residual amounts of surfactant remaining on the surface. The presence of the C—H absorption bands confirms the continued presence of the organic substituent in the particles. In particular, the spectrum of the phenyl-silica contains four summation bands at 1960, 1890, 1924 and 1772 $cm^{-1}$, which are typical of a monosubstituted phenyl ring.

Figure 21:
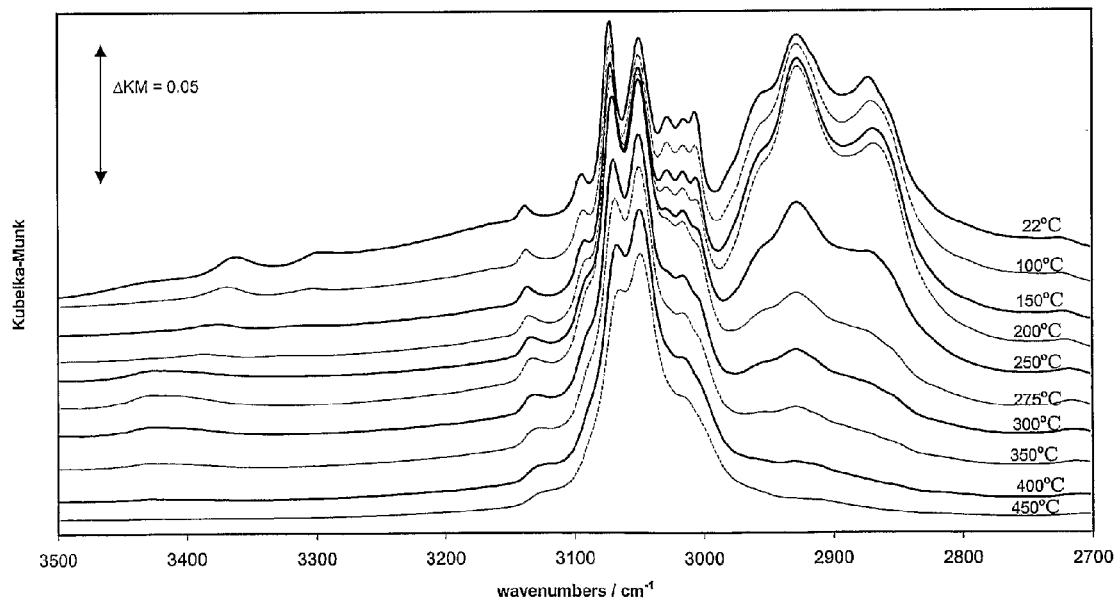
FIG. 21 shows variable temperature (22-450° C.) DRIFT spectra of a PTMS product according to the present invention, over the spectral range 2700-3500 cm$^{-1}$.

Amine groups contribute only weakly to the spectra, as two N—H stretching bands at 3367 and 3302 cm$^{-1}$, which are present in the spectra all of the organo-silica species shown here. These bands are typically weak in IR, and so it is difficult to estimate the amount of amine incorporation by this means. FIG. 21 shows spectra in the region 3500-2700 cm$^{-1}$ which contains the N—H and C—H stretching modes of the amine and organic fractions. The two amine stretching bands are observed to shift progressively to higher energy with heating from 22 to 200° C. At 250° C., the bands occur at 3427 and 3408 cm$^{-1}$. This sudden shift coincides with the appearance of broad C=O absorption at about 1705 cm$^{-1}$ (not shown). Both observations suggest that the amines are oxidised at 250° C. to form —(CH$_2$)$_2$—C(=O)—NH$_2$. This oxidised amine (amide) is then removed over the temperature range 300-450° C. Adsorbed surfactant can be monitored using the NP-9 absorption band at 1510 cm$^{-1}$ (not shown). The surfactant was removed on heating between 200 and 300° C.

The alkyl C—H stretching modes (3000-2800 cm$^{-1}$) which are dominated by the —CH$_2$— vibrations of propylamine and surfactant, are completely removed by 450° C. The phenyl modes (3200-3000 cm$^{-1}$) are not significantly reduced in intensity on heating over this temperature range, although there are some shifts and broadening observed. Cooling the sample from 450° C. to ambient temperature reinstates the original spectrum, but without the presence of the alkyl C—H bands or N—H stretching modes.

Encapsulation Efficiency

The encapsulation efficiency depends on the molecule being encapsulated, the precursor used, and the concentration of ormosil in the emulsion. Table 2 contains the typical encapsulation efficiencies of a number of dopants in the various organo-silicas. Some sample-to-sample variability has been noted where the synthesis has been repeated multiple times, and this is shown in the table as a range of values. Increasing the ormosil:water concentration from 1:25 to 2:25 results in increased encapsulation efficiencies for all samples trialled. Encapsulation efficiencies observed for solvent blue 35 dye encapsulated in particles formed from 50/50 mixtures of ormosil and alkoxide were similar to those found using 100% ormosil precursors (about 45-65%). Thus, this is a convenient means of accessing smaller particle sizes for applications which require them, without sacrificing significant encapsulation efficiency.

TABLE 2

Encapsulation efficiencies for various dopants in organosilicas.

| Hydrophobe | Precursor | surfactant | Reactant: water (v/v) | Encapsulation efficiency (%) | Method |
|---|---|---|---|---|---|
| Solvent blue 35 | VTMS | NP9 | 1:25 | 25-52 | UV |
| | VTMS | NP9 | 2:25 | 71 | UV |
| | PTMS | NP9 | 1:25 | 30-64 | UV |
| | PTMS | NP9 | 2:25 | 85 | UV |
| | ETMS | NP9 | 1:25 | 53 | UV |
| | VTMS | Triton X-100 | 1:25 | 52 | UV |
| | VTMS | Triton X-114 | 1:25 | 39-53 | UV |
| | ETES | NP9 | 1:25 | 60 | UV |
| | VTMS/TMOS | NP9 | 1:25 | 46 | UV |
| | VTMS/TEOS | NP9 | 1:25 | 42 | UV |
| | PTMS/TMOS | NP9 | 1:25 | 63 | UV |
| | PTMS/TEOS | NP9 | 1:25 | 56 | UV |
| | PTMS + 2 wt % EC7* | NP9 | 1:25 | 80 | UV |
| | PTMS + 5 wt % EC7 | NP9 | 1:25 | 80 | UV |
| | PTMS + 10 wt % EC7 | NP9 | 1:25 | 78 | UV |
| | PTMS + 2 wt % EC45# | NP9 | 1:25 | 71 | UV |
| | VTMS + 2 wt % EC45 | NP9 | 1:25 | 56 | UV |
| | ETMS + 2 wt % EC45 | NP9 | 1:25 | 52 | UV |
| Sudan red | PTMS | NP9 | 1:25 | 41-54 | UV |
| | VTMS | NP9 | 1:25 | 15-95 | UV |
| | ETMS | NP9 | 1:25 | 21 | UV |
| | PTMS/TEOS | NP9 | 1:25 | 44 | UV |
| limonene | VTMS | NP9 | 1:25 | 16 | HPLC |
| | VTMS | NP9 | 2:25 | 20 | HPLC |
| | PTMS | NP9 | 1:25 | 14 | HPLC |
| | PTMS | NP9 | 2:25 | 19 | HPLC |
| | VTMS | TritonX100 | 1:25 | 12 | HPLC |
| | VTMS | TritonX114 | 1:25 | 23 | HPLC |
| retinol | PTMS | NP9 | 1:25 | 44-56 | UV |

*EC7 = ethylcellulose, av. viscosity = 7 mPa · s, (5% soln in toluene:ethanol 80:20)
EC45 = ethylcellulose, av. viscosity = 45 mPa · s, (5% soln in toluene:ethanol 80:20)

Cross-Section—Transmission Electron Microscopy of Particles

It appears that reaction of the ormosil with the condensation catalyst is not an interfacial one but occurs in the bulk of the oil droplet, due to the miscibility of the catalyst with the hydrophobic ormosil. Thus, it is expected that a solid, as opposed to a hollow, sphere is likely to be produced. This was confirmed by cross-section TEM. Limonene-doped particles were prepared using a 2:25 (v/v) ormosil:water reaction with APTES. The reason for using the increased concentration is to produce a larger particle size range for investigation.

The silica microspheres were embedded in an epoxy resin and cured overnight at 35° C. The embedded blocks were trimmed and sectioned with a Leica UCT Ultramicrotome at room temperature. Approximately 80 mm ultra-thin sections were obtained and placed on holey carbon coated copper EM grids. The sections were examined at 200 kV with a JEOL 2000FXII Transmission Electron Microscope (TEM).

Figure 22:
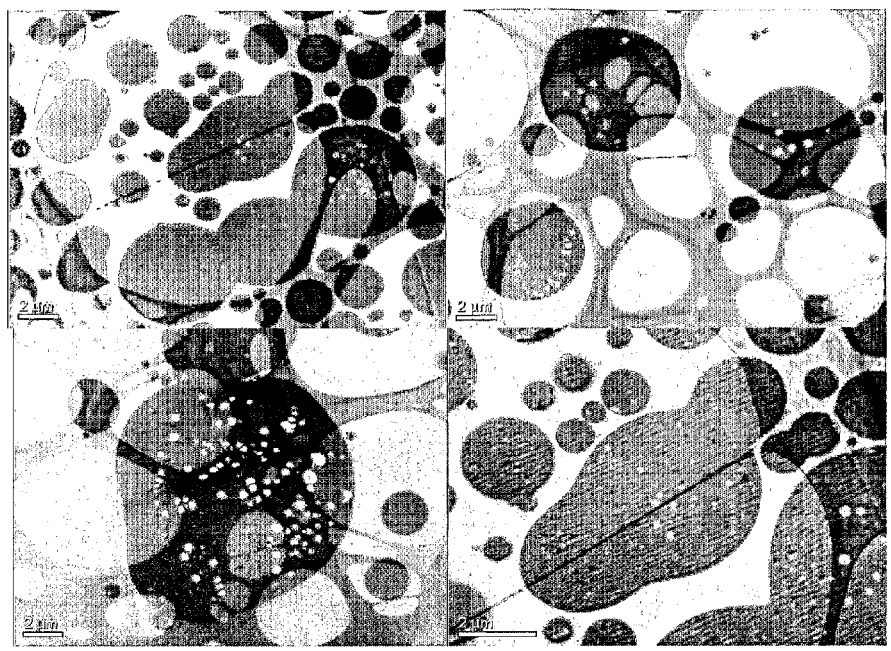
FIG. 22 shows TEM images (size bar=2 micron) of cross-sectioned limonene-doped VTMS particles according to the invention, imbedded in epoxy resin.

The diameters of the particles were found to range dramatically in size, from approximately 0.1-40 μm. FIG. 22 shows four different images of the cross-sections, illustrating the size and morphology of the organosilica microspheres. The striations (alternating light and dark areas) that can be seen on the microspheres appear to be a preparation artefact due to compression of the microspheres as they were microtomed. There was no obvious change in the structure of the microsphere from side to side: no evidence of an outer shell was observed. A number of the microspheres contained vacuoles which presumably still contained, or had previously, contained limonene. The oil vacuoles are distributed randomly throughout the matrix.

Solid State $^{29}$Si NMR $^{29}$Si NMR spectra of the three types of particle prepared according to the present invention (vinylsiloxane, phenylsiloxane and ethylsiloxane) were investigated in order to quantify the extent of incorporation of aminopropylsiloxane in the products. Elemental analysis by Ottenbrite et al ('Self-catalysed synthesis of organo-silica nanoparticles'; R. M. Ottenbrite, J. S. Wall, J. A. Siddiqui, *J. Am. Ceram. Soc.*, 83 (12), 3214-15, 2000) suggested that incorporation of amine species is minor only, at least in particles formed from VTMS, with up to 10% of Si having bound amine groups.

Experimental

High resolution solid-state $^{29}$Si magic-angle-spinning (MAS) NMR spectra were acquired at ambient temperature using an MSL-400 NMR spectrometer ($B_o$=9.4 T) operating at the $^{29}$Si frequency of 79.48 MHz. All $^{29}$Si MAS NMR data were acquired using a Bruker 7 mm double-air-bearing probe with cross-polarisation (CPMAS) and single pulse (Bloch decay) methods, both of which utilised high-power $^1$H decoupling during data acquisition. The MAS frequencies implemented for these measurements were ~5 kHz. For the $^{29}$Si CPMAS experiments a recycle delay of 5 s, a $^1$H-$^{29}$Si Hartmann-Hahn contact period of 5 ms and an initial $^1$H π/2 pulse width of 5 μs were common to all CPMAS data. For the corresponding $^{29}$Si MAS single pulse/high-power $^1$H decoupling measurements, a single $^{29}$Si π/4 pulse width of 2.5 μs was used in conjunction with recycle delays of 30-60 s for quantitative $^{29}$Si measurements. All $^{29}$Si MAS and CPMAS chemical shifts were externally referenced to tetramethylsilane (TMS) via a high purity sample of kaolinite, which was also used to establish the $^1$H-$^{29}$Si Hartmann-Hahn condition.

Results

Figure 23:
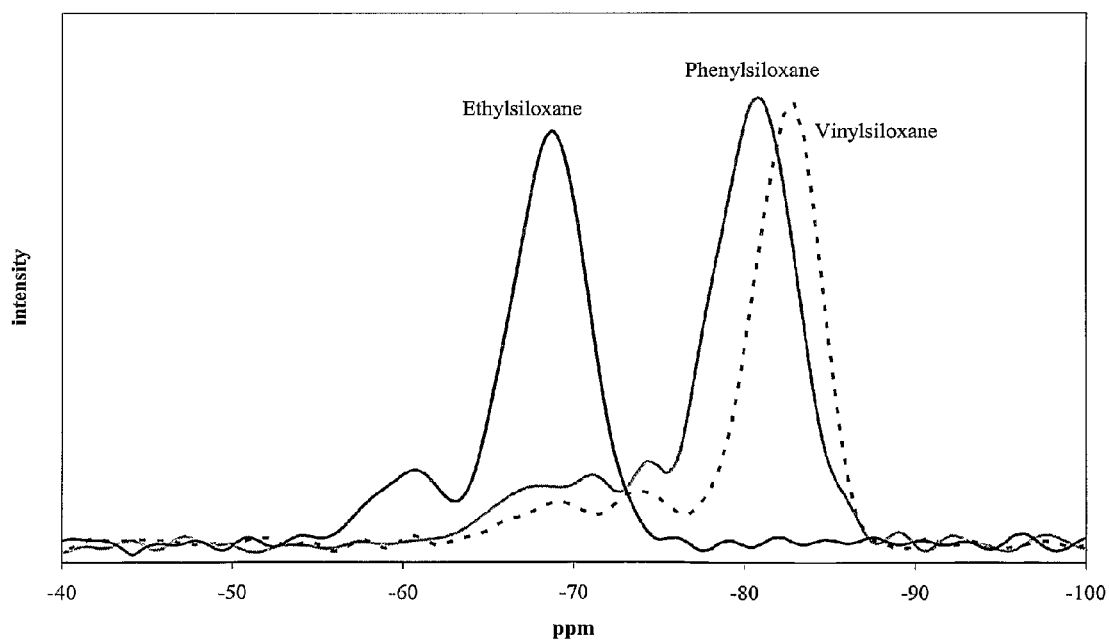
FIG. 23 shows $^{29}$Si High Power Decoupled NMR (Nuclear Magnetic Resonance) spectra of ethylsiloxane (---), phenylsiloxane (-) and vinylsiloxane (---)

The High power decoupled (HPDEC) spectra and the deconvolution results are shown in FIG. 23 and Table 3 respectively.

TABLE 3

Deconvolution of $^{29}$Si HPDEC spectra - peak positions and peak area (as % of total abundance).

| Precursor | Peak centre (ppm) | % total area (abundance) |
|---|---|---|
| VTMS | 82.5 | 84.6 |
|  | 73.9 | 6.7 |
|  | 69.1 | 6.2 |
|  | 66.4 | 2.5 |
| PTMS | 80.6 | 84.5 |
|  | 74.2 | 2.3 |
|  | 71.1 | 4.9 |
|  | 67.2 | 8.2 |
| ETMS | 68.6 | 85.3 |
|  | 60.3 | 14.7 |

Ideally, up to four peaks are expected for each sample. Two correspond to the $T_3$ and $T_2$ species formed from the alkyltrimethoxysilane precursor, and a further two to $T_3$ and $T_2$ species from aminopropyltriethoxysilane which are also possibly incorporated. $T_n$ denotes the extent of condensation, with n being the number of siloxanes bound to a central Si.

The $T_2$ and $T_3$ peaks of vinylsiloxane, phenylsiloxane and ethylsiloxane have been identified by comparison with the $^{29}$Si spectra reported by Arkhireeva and Hay ('Synthesis of sub-200 nm silsesquioxane particles using a modified Stöber sol-gel route', A. Arkhireeva, J. N. Hay, *J. Mater. Chem.*, 13, 3122-3127, 2003). While the absolute peak positions varies by up to about 2 ppm, the $T_2$-$T_3$ separation is expected to be similar. On this basis, the 82.5 and 73.9 ppm peaks of the VTMS-derived sample are assigned to $T_3$ and $T_2$ of respectively of vinylsiloxane. Thus, the remaining peaks at 69.1 and 66.4 peaks are assigned to amine species, with a combined intensity of 8.7%. In the case of the sample prepared from PTMS, at least the peak at 67.2 ppm is attributable to an amine species, with an intensity of 8.2%. In the case of the sample prepared from ETMS, the amine peaks are not separately resolved from the ethylsiloxane, as may be expected given the similarity of the $H_2N$—$(CH_2)_3$— and $CH_3$—$CH_2$— substituents.

Although the $^{29}$Si NMR spectra are not sufficiently well-resolved to give definitive values for the amount of amine present, the spectra of the VTMS and PTMS products support previously reported results of up to 10 mol % amine being incorporated in the particles.

CHN Microanalysis

The amine content of phenyl, vinyl and ethylsiloxane particles was estimated from the CHN content, measured using a Carlo Erba 1106 automatic analyser. The amount of water associated with the particles was measured before drying and found to be <5 wt %. The particles were then dried at 60° C. for 6 days before analysis. The extent of amine incorporation was estimated using the N content, as there is C and H present in the organo-substituent in the particles. In addition, there is likely to be a small amount (<2 wt %) of surfactant absorbed on the particles, which contains C and H but not N. The results are represented in table 4.

TABLE 4

CHN composition of ethyl, vinyl and phenylsiloxane.

| Organo-substituent | C (%) | H (%) | N (%) | Amine content (wt %) | Amine content (mol %) |
|---|---|---|---|---|---|
| ethyl | 44.58 | 7.14 | 3.33 | 26.2 | 20.7 |
| vinyl | 33.79 | 4.63 | 0.88 | 6.9 | 5.2 |
| phenyl | 55.06 | 4.96 | 0.98 | 7.7 | 8.9 |

The amine content calculated for phenylsiloxane is very close to the value obtained by $^{29}$Si NMR, whereas that for vinylsiloxane is somewhat smaller, at 5.2 mol %. The amount of amine incorporated in the ethylsiloxane is considerably higher than in the other organosilicas, at 20.7 mol %. This is consistent with the larger amount of product obtained for this material (see table 1).

Organosiloxane Stability in Base

Figure 24:
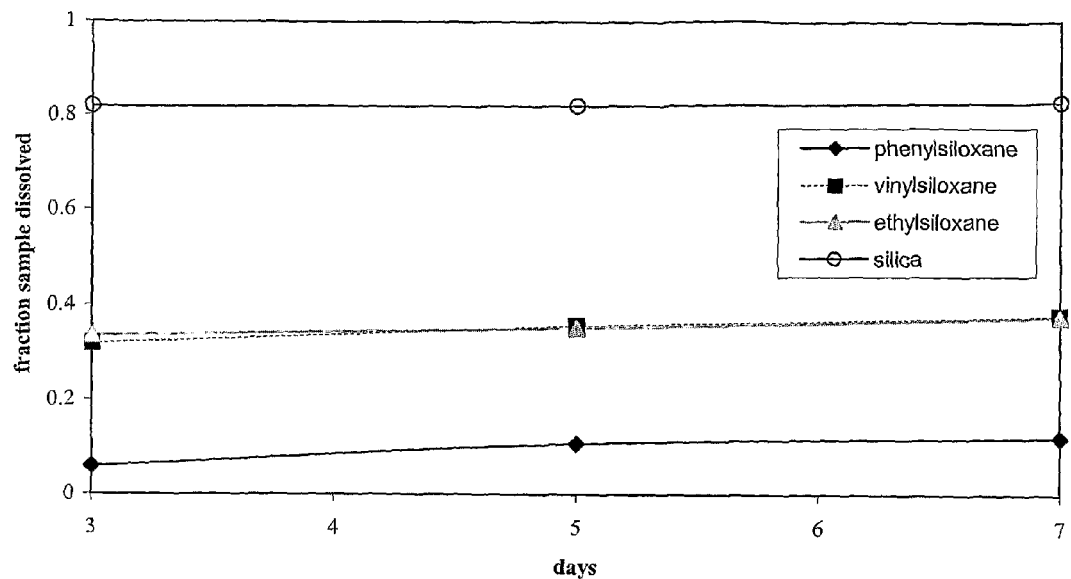
FIG. 24 shows a graph illustrating the fraction of sample dissolved at pH=12 with time, for ♦-phenylsiloxane, --■-- vinylsiloxane, -▲-ethylsiloxane, and -o-silica.

The rate of dissolution of organosiloxane particles over one week at pH=12, was compared with that of unmodified silica (100 μm spheres). 10-20 mg of solid was suspended in NaOH solution (0.01 mol dm$^{-3}$, 100 mL) and shaken continuously for one week at ambient temperature. On day 3, 5 and 7, supernatant (10 mL) was separated from each sample and analysed by Inductively Coupled Plasma Atomic Emission Spectroscopy (ICP-AES) for Si content. The fraction of dissolved sample is shown in FIG. 24 for the silica, phenylsiloxane, vinylsiloxane and ethysiloxane samples.

As expected, the unmodified silica dissolved relatively rapidly at pH=12. Although the organosilicas (i.e. phenylsiloxane, vinylsiloxane and ethysiloxane) tested had a significantly smaller particle size (about 200 nm average size vs 100 μm for the silica sample), dissolution was considerably slower, with the phenylsiloxane samples showing the slowest dissolution at about 12% dissolved after one week.

EXPERIMENTAL EXAMPLES

Example 1

Retinol (Vitamin A) Encapsulated in Phenylsiloxane Particles

Synthesis

Retinol (210 mg) was slowly dissolved into 1.25 g NP-9 with stirring, followed by addition of distilled water (25 mL). Phenyltrimethoxysilane (1 mL) was added to the mixture and stirred for five minutes. Finally, 3-aminopropyltriethoxysilane (1 mL) was added and the solution left stirring overnight. The following day, the solid was removed by centrifugation (10,000 rpm, 10 minutes) and washed twice with water. After the final centrifugation, the solid was allowed to dry at ambient temperature, in the absence of light. The encapsulation efficiency was estimated to be 56%, by measuring the visible absorbance of the supernatant, reserved after separating and washing the solid. The loading of retinol was calculated to be 14% (w/w).

Characterisation

Figure 25:
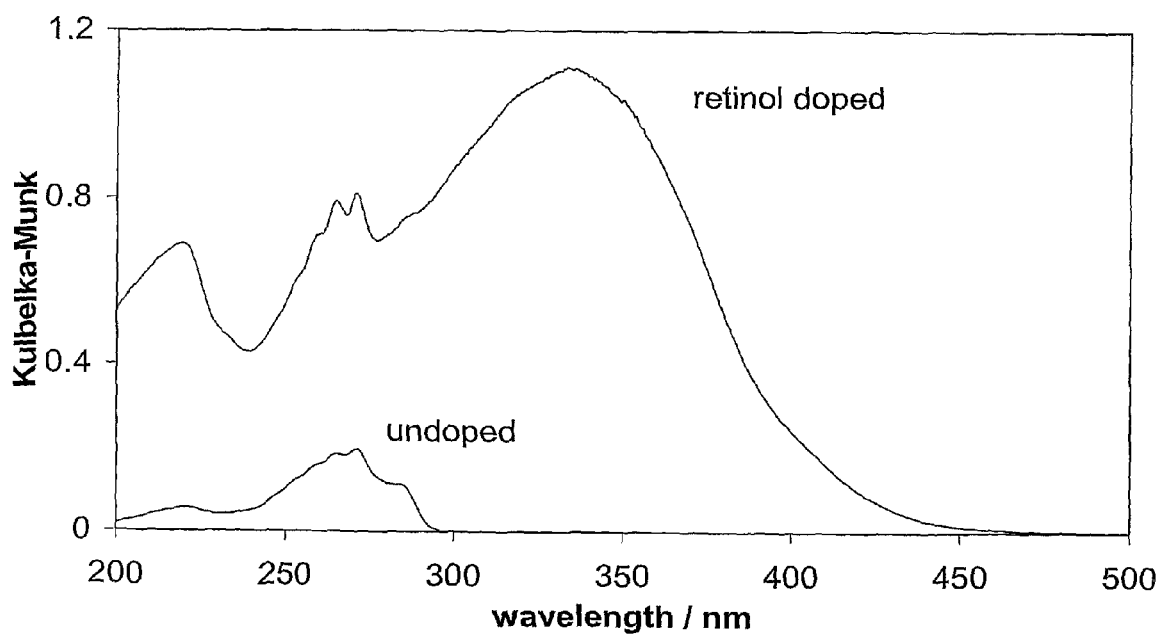
FIG. 25 shows UV/Visible diffuse reflectance spectra of retinol-doped and undoped phenylsiloxane particles formed using a process according to the present invention.

The UV/Visible spectra of the both retinol-doped and undoped phenylsiloxane particles dispersed in PTFE powder (10 wt %), were collected using a diffuse reflectance accessory. FIG. 25 shows that the retinol-loaded sample has a strong absorption band at 335 nm. The undoped sample shows weaker peaks at 266, 272, and 284 nm, due to the phenyl ring in the organosilica matrix. Immersion of retinol-doped powder in ethanol results in the partial release of retinol, as observed by a characteristic absorption peak at 325 nm. This indicates that the retinol molecule has not been damaged by the encapsulation process. The bandshift from 325 nm in ethanol solution to 335 nm in the solid is due to difference of environment experienced by the retinol molecule.

Figure 26:
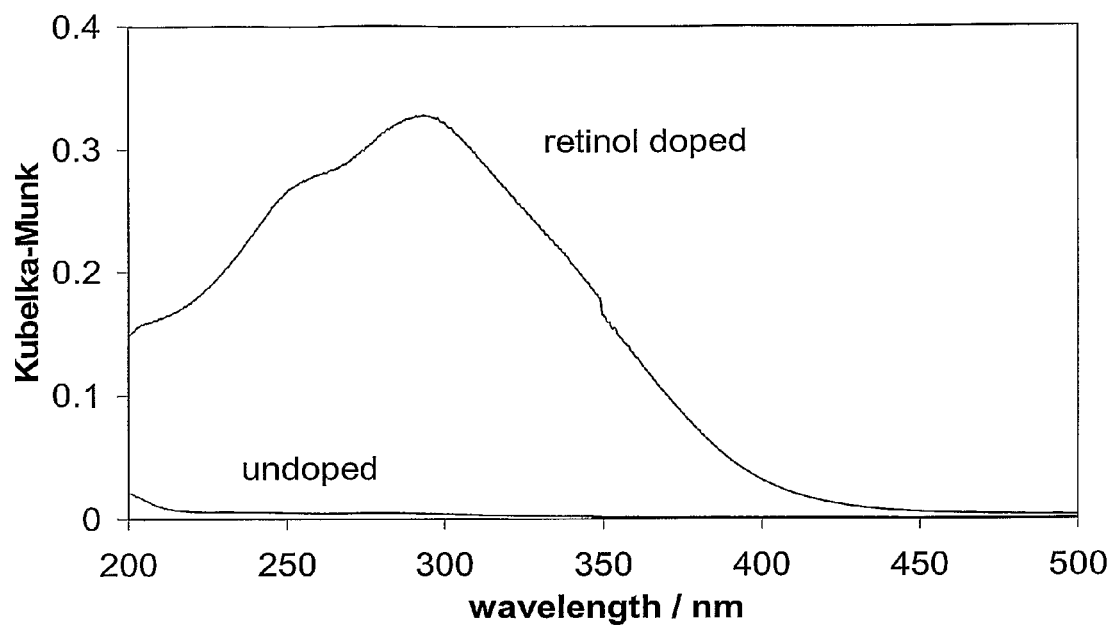
FIG. 26 shows UV/Visible diffuse reflectance spectra of retinol-doped and undoped silica particles formed using a double emulsion process.

In contrast, retinol doped into silica particles made using a double emulsion process using TMOS as a silica precursor shows a peak at 292 nm (see FIG. 26). Subsequent leaching of the encapsulated retinol into ethanol does not show a peak at 325 nm, indicating that the retinol has been degraded by the encapsulation process. This is likely to be due to exposure to low pH (=1.0) during the hydrolysis of TMOS.

Figure 27:
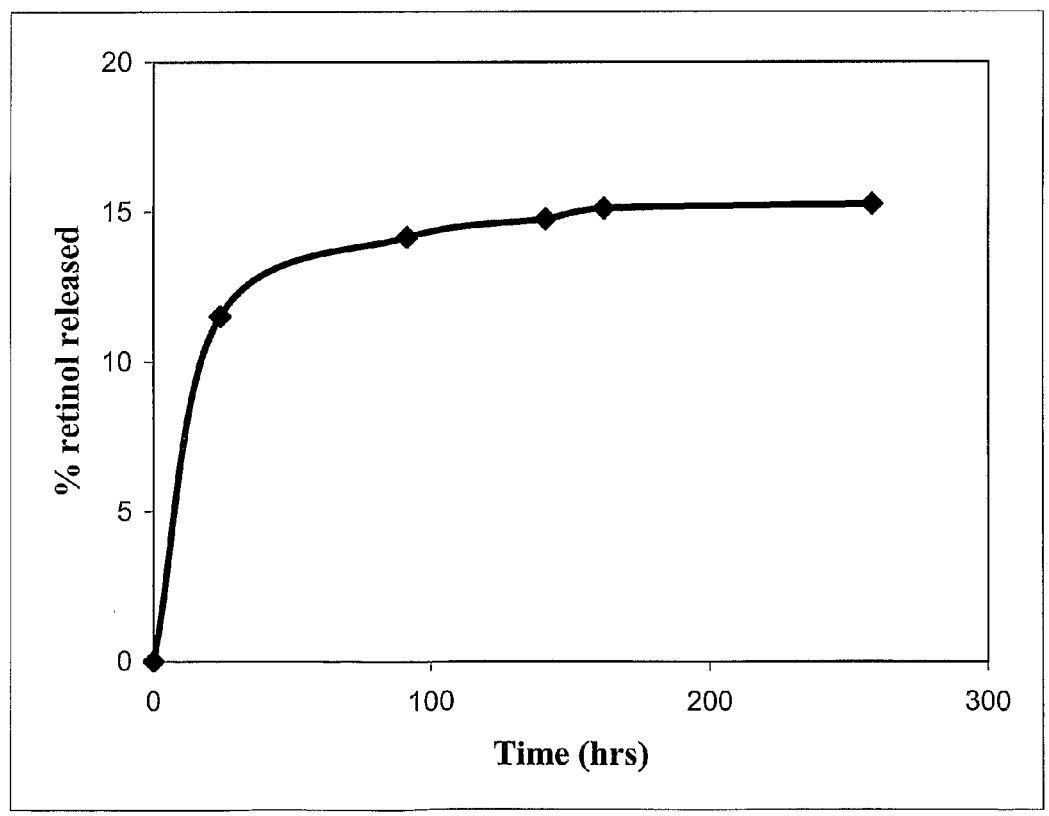
FIG. 27 is a graph showing release of retinol from phenylsiloxane particles into 50/50 v/v ethanol/water over time.

Release of retinol from the particles into 50:50 (v/v) ethanol:water solution was measured over a period of 11 days. Due to decomposition of retinol released into the solution, the supernatant was refreshed at each time point, and the release measured using UV/Vis spectroscopy (peak at 325 nm). The cumulative release curve is shown in FIG. 27. Approximately 11% of the encapsulated retinol was released after one day, followed by slower release thereafter.

Example 2

Encapsulation of Rhodamine 6G in Phenylsiloxane Particles

The synthesis method described in the present specification is suited to encapsulation of hydrophobic molecules. However, hydrophilic molecules such as rhodamine 6G also may be encapsulated.

Synthesis

Rhodamine 6G dye (40 mg) was stirred into NP-9 (2.5 g) for 5 minutes. 50 g of distilled water was then added and stirred for 10 minutes. Phenyltrimethoxysilane (2 mL) was added and a cloudy mixture formed, which was stirred for 6 minutes. Finally, 3-aminopropyltriethoxysilane was added and the mixture left to stir overnight. The following day, the solid was separated and washed twice with water, using centrifugation (10,000 rpm, 10 minutes) to remove supernatant. The supernatant was highly coloured, indicating that the encapsulation efficiency was relatively low.

Release into Water

Figure 28:
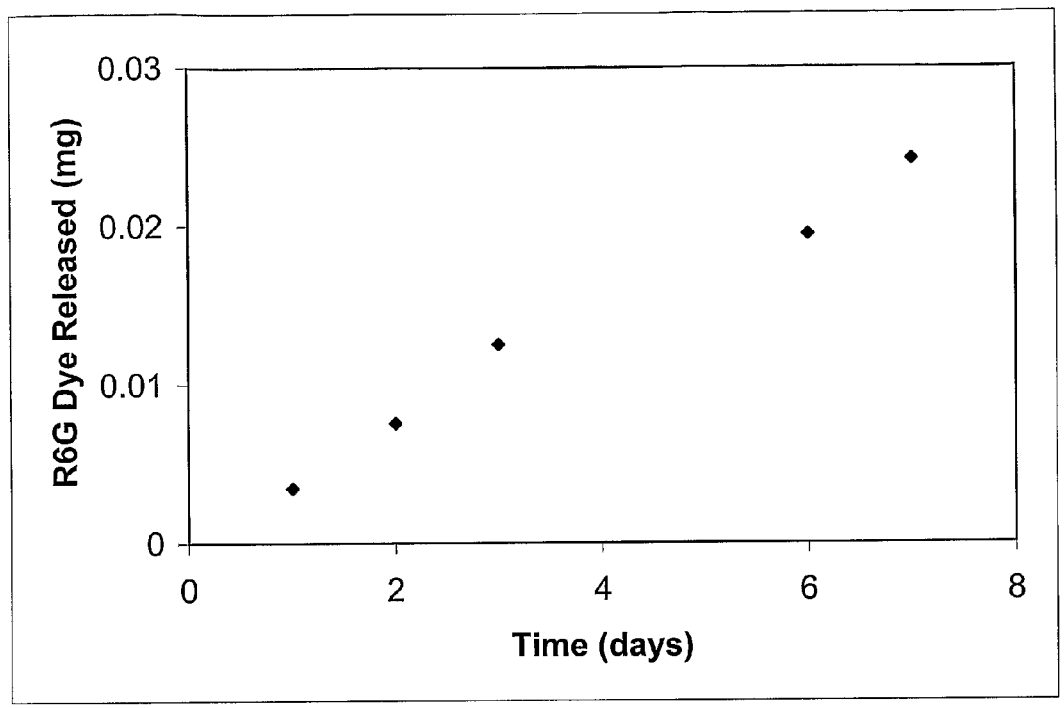
FIG. 28 is a graph showing the amount of Rhodamine 6G dye released from phenylsiloxane particles into water over time.

The solid was immersed in approximately 40 mL water and stirred to mix. Over a period of one week, the supernatant was removed daily for UV/Vis analysis and replaced with fresh water. The total weight of rhodamine 6G released with time is shown in FIG. 28. After one week the particles remained coloured, indicating that only a small proportion of the encapsulated material had been released over this time.

Example 3

Encapsulation of Diuron into Organosilicon Particles

Figure 29:
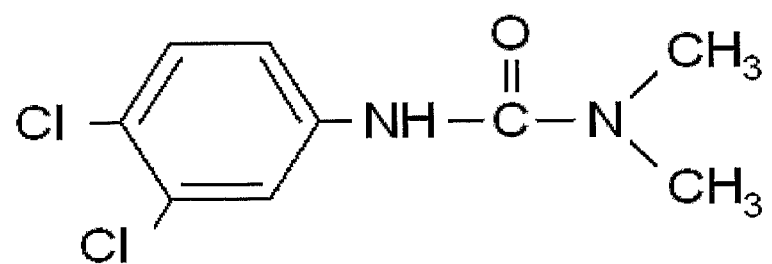
FIG. 29 shows the chemical structure of diuron.

Diuron (see FIG. 29) was encapsulated into phenylsiloxane and vinylsiloxane particles for release into sodium hydroxide solution at pH=12.

Synthesis 280 mg Diuron was stirred into two 5 wt % NP-9 solutions (25 mL) for 8 hours. Phenyltrimethoxysilane (2 mL) was added to the first solution and vinyltrimethoxysilane (2 mL) was added to the second with stirring, followed by addition of 3-aminopropyltriethoxysilane (2 mL). The solutions were stirred overnight, then separated and washed twice with water using centrifugation (10,000 rpm, 10 minutes) to remove the supernatant.

Characterisation

Figure 30:
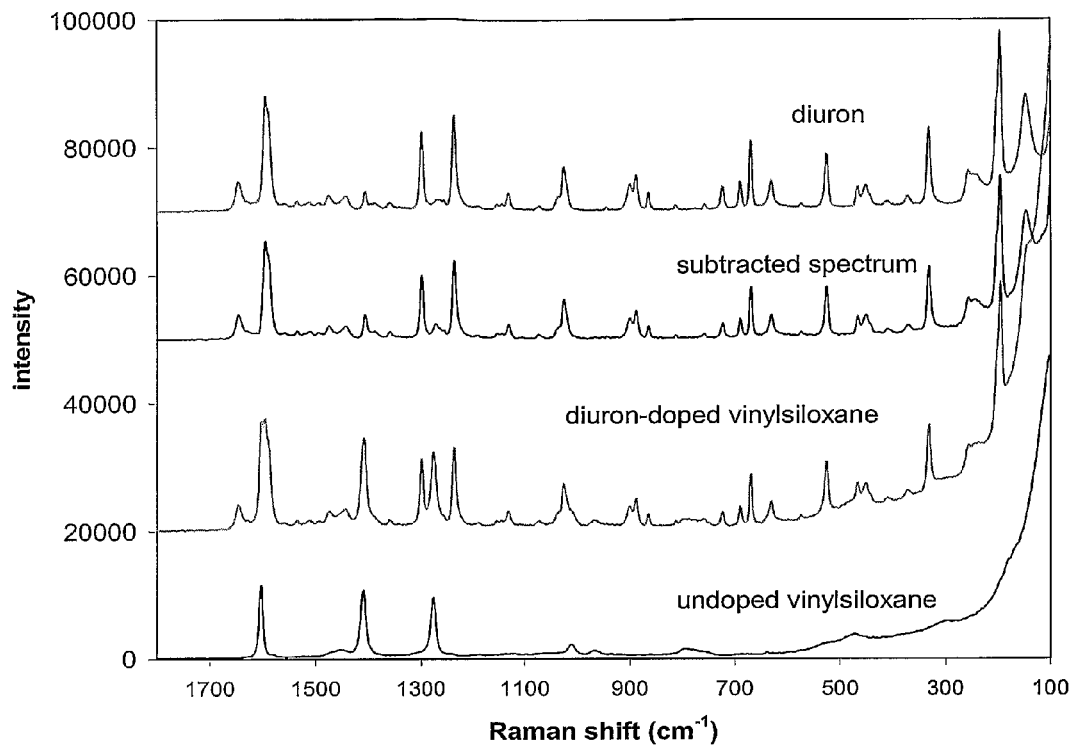
FIG. 30 shows Raman spectra of undoped vinylsiloxane, diuron-doped vinylsiloxane, subtracted spectrum (diuron-doped vinylsiloxane, where the undoped vinylsiloxane bands have been subtracted) and diuron.

The encapsulation efficiency was estimated to be 92% (7 and 11 wt % loading for phenylsiloxane and vinylsiloxane respectively), based on analysis of diuron concentration in the supernatant by HPLC. The Raman spectra of the undoped and diuron-doped vinylsiloxane particles are shown in FIG. 30. Vinylsiloxane was analysed by Raman in preference to phenylsiloxane due to expected overlap of the phenyl group vibrations with those of diuron. The spectral bands of undoped vinylsiloxane were subtracted from those of the diuron-doped material. The resulting spectrum is denoted 'subtracted spectrum' on FIG. 30, and shows good agreement with the spectrum of neat diuron, consisting mostly of phenyl ring and C=O vibrations, confirming the successful encapsulation of diuron in the particles.

Release

Figure 31:
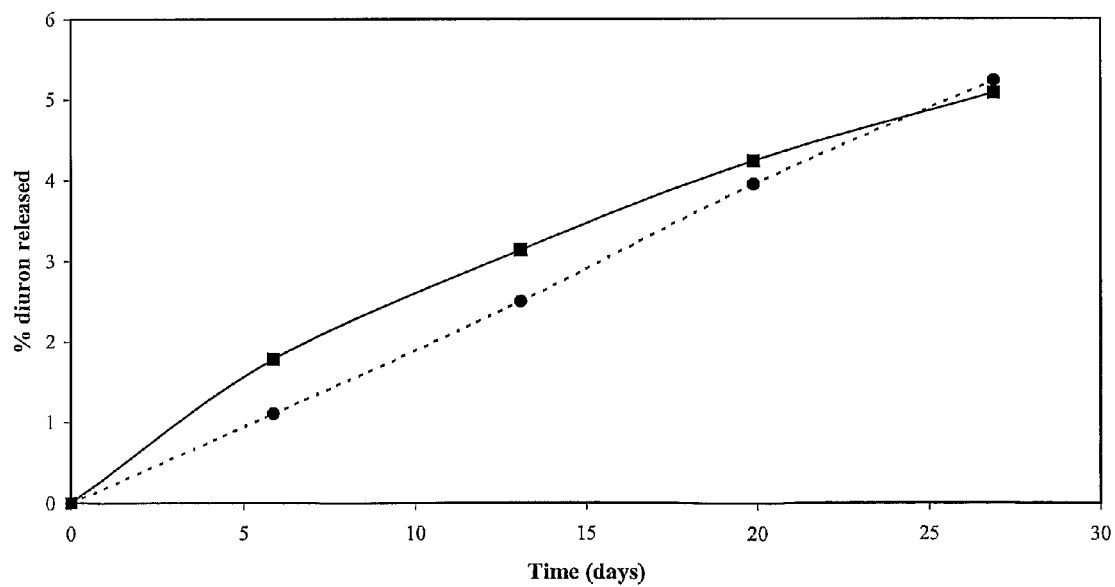
FIG. 31 is a graph showing release of diuron from phenylsiloxane (-■-) and vinylsiloxane (--●--) particles into sodium hydroxide solution (at pH=12) over time.

The rate of release of diuron into sodium hydroxide solution at pH=12 was measured over a period of one month. Analysing the extent of release is somewhat problematic due to the low solubility of diuron in water. In order to determine the release characteristics, diuron-doped particles (about 150 mmol) were suspended in NaOH solution (0.01 mol dm$^{-3}$, 50 mL) and stirred. At one-week intervals, the solution was centrifuged and the supernatant removed. The diuron-doped particles were then resuspended in a fresh solution of NaOH (0.01 mol dm$^{-3}$, 50 mL) and stirred. The removed supernatant was shaken with octanol (10 mL) in a separating flask to extract dissolved diuron. This was repeated twice, and the resulting approximately 30 mL organic fraction was reserved for diuron analysis by HPLC. The release curve is shown in FIG. 31. The amount of diuron released after 27 days was about 5% (of the total encapsulated) for both samples. The amount released was less than expected compared with the dissolution results at pH=12. This could reflect an incomplete extraction of diuron from the aqueous phase during the process of shaking with octanol.

Example 4

Effect of Reaction Time

Figure 32:
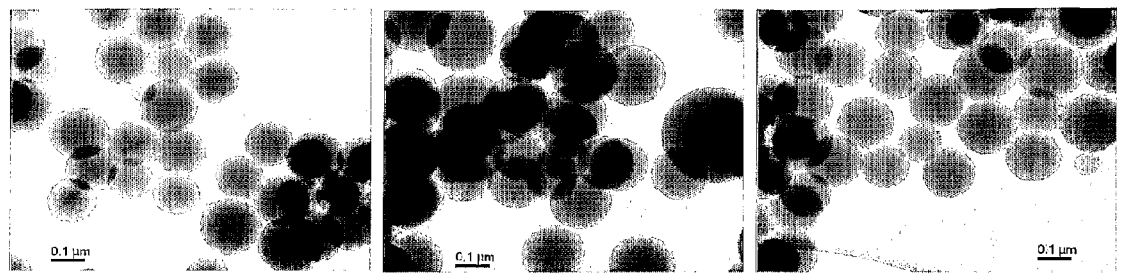
FIG. 32 shows TEM images (size bar=100 nm) of 2 (left image), 4 (centre image) and 7.5 (right image) hour reaction products.

In this example, the effect of reducing the reaction time from the typical overnight reaction on the particle size and morphology, and the yield of product was investigated. As the interest was in formation of the host matrix rather than encapsulation, no additional hydrophobe was added to the reaction mixture in these experiments.
Synthesis Reactions were conducted using the same basic procedure: 1 mL of phenyltrimethoxysilane was added to 25 mL of 5 wt % NP-9 solution and stirred for 10 minutes, followed by addition of 1 mL of 3-aminopropyltriethoxysilane. The opaque solutions were stirred for varying amount of times: 2, 4 and 7.5 hours. The samples were removed after the specified time, and the solids separated by centrifugation (10,000 rpm, 10 minutes), and washed three times with distilled water. The solids were characterised by TEM, and the products dried for 64 hours under nitrogen to compare the final weights obtained.
Results In the case of the 4 and 7.5 hour reaction times, the products dried to a free-flowing powder. However, the product from the two hour reaction remained tacky, and had not fully dried. This suggests that two hours was not sufficient time to fully complete the condensation of the phenyltrimethoxysilane. The weight of the products is recorded in Table 5, including a value of 0.806 g for a reaction conducted over 17 hours (i.e. the typical synthesis period). TEM images of the products are shown in FIG. 32. In all cases, spherical particles were obtained. No significant difference in size (average about 150 nm) and shape was noted in particles formed after the various reaction times.

TABLE 5

Weights of phenylsiloxane (dried 64 hours) after nominated reaction time.

| Reaction time (hours) | Yield of sample (g) | % of standard yield |
|---|---|---|
| 2 | 0.920* | — |
| 4 | 0.680 | 84% |
| 7.5 | 0.733 | 91% |
| 17 | 0.806 | 100% |

*sample tacky - not fully dried

In conclusion, reaction times can be reduced from the typical overnight reaction.

Example 5

Release of Solvent Blue Dye from Phenylsiloxane Particles

Synthesis

Figure 33:
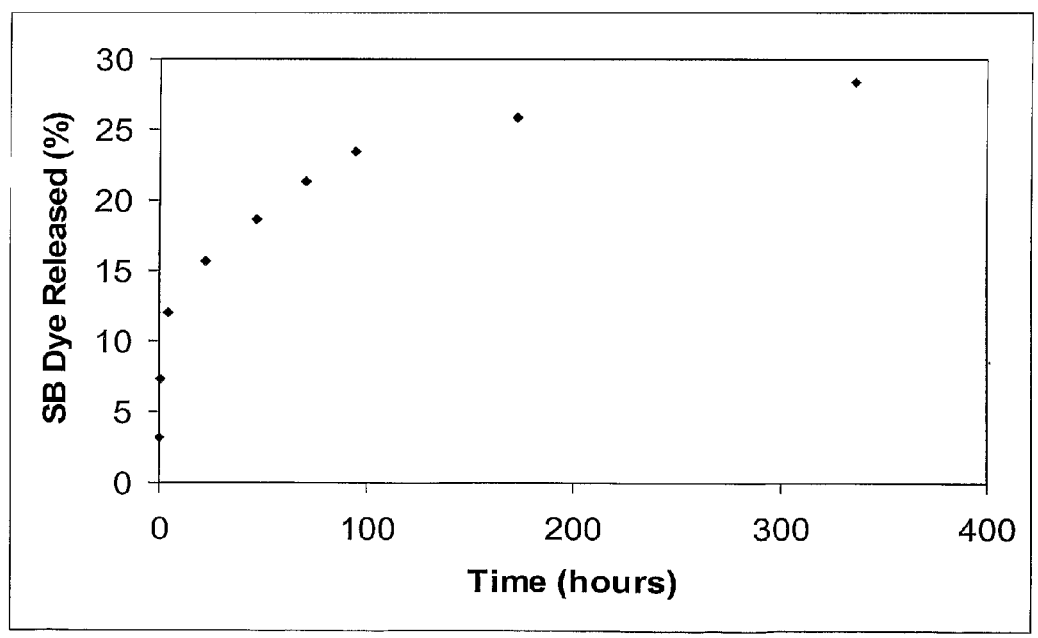
FIG. 33 is a graph showing release of solvent blue 35 dye from phenylsiloxane particles into 50/50 v/v ethanol/water over time.

Solvent Blue 35 dye powder (4.0 mg) was added to NP-9 (2.5 g) and stirred. Distilled $H_2O$ (50 mL) was then added to the surfactant mixture, with stirring. Phenyltrimethoxysilane (2 mL) was added and stirred for five minutes, followed by addition of 3-aminopropyltriethoxysilane. The sample was stirred overnight, after which the solid was separated by centrifugation (10,000 rpm, 10 minutes), and washed twice with distilled water. The encapsulation efficiency was determined to be 58% by analysis of the supernatant removed by centrifugation (approximately 0.14 wt % loading).
Release The sample was suspended in 50/50 v/v ethanol/water (10 mL) with stirring. At each time point, the sample was centrifuged (10,000 rpm, 10 minutes) and the supernatant removed. Fresh solvent was then added and the solid resuspended. The release curve is shown in FIG. 33. In comparison, the release of dye from a similar sample into 100% ethanol solution is very rapid, with about 40% of the dye released after several minutes.

Example 6

Release of Sudan Red Dye from Phenylsiloxane Particles

Synthesis

Figure 34:
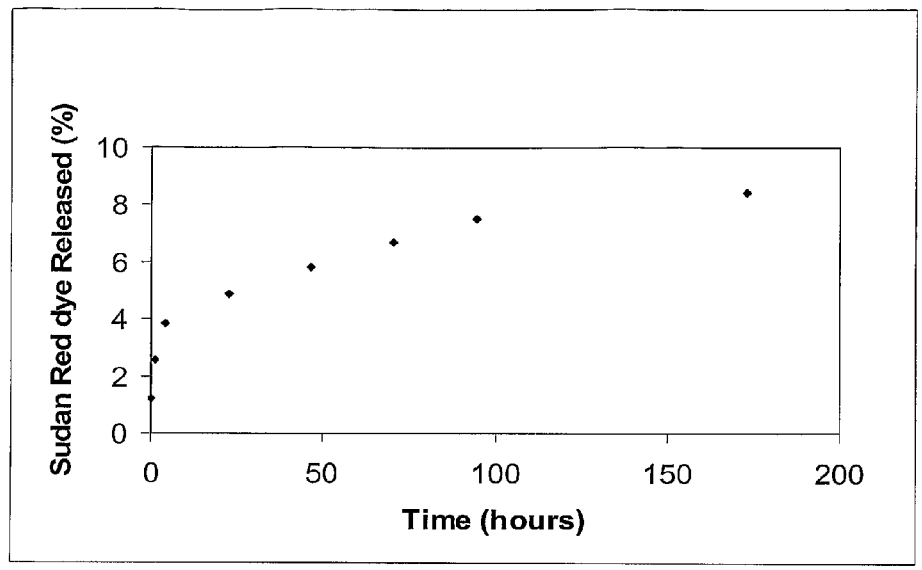
FIG. 34 is a graph showing release of sudan red dye from phenylsiloxane particles into 50/50 v/v ethanol/water over time.

Sudan red dye (2 mg) was stirred into NP-9 (1.25 g). Distilled water (25 mL) was added with stirring. Phenyltrimethoxysilane (1 mL) was added and stirred for 5 minutes, followed by addition of 3-aminopropyltriethoxysilane. The sample was stirred overnight, and the resulting solid separated by centrifugation (10,000 rpm, 10 minutes), and washed twice with distilled water. The encapsulation efficiency was determined to be 58% by analysis of the supernatant removed by centrifugation (approx. 0.14% loading).
Release The sample was suspended in 50/50 v/v ethanol/water (10 mL) with stirring. At each time point, the sample was centrifuged (10,000 rpm, 10 minutes) and the supernatant removed. Fresh solvent was then added and the solid resuspended. The release curve is shown in FIG. 34. In contrast to the slow release into ethanol/water, the release into ethanol is very rapid, with approximately 70% of the encapsulated dye released within one hour.

Example 7

Release of Sudan Red Dye from Vinylsiloxane Particles

Synthesis

Figure 35:
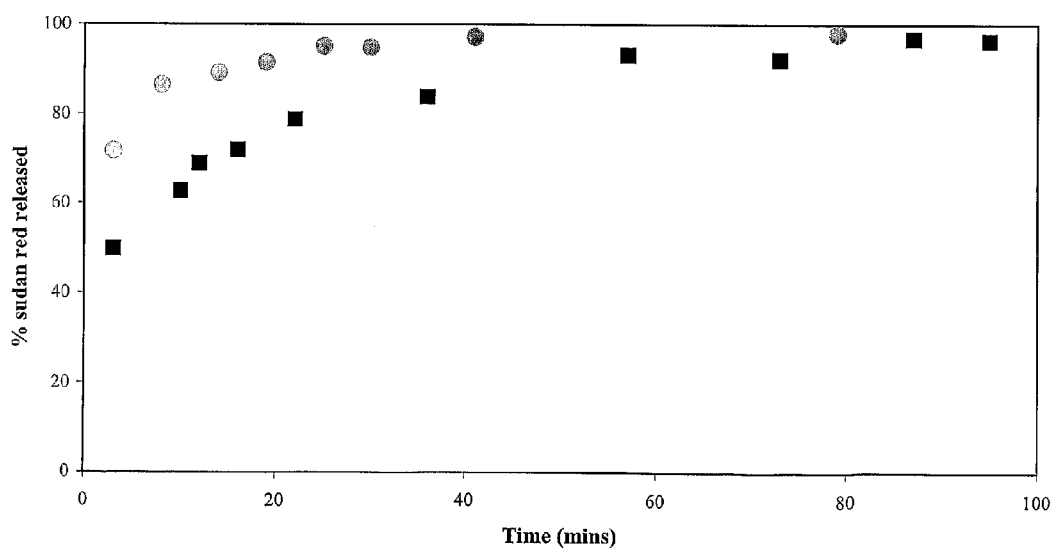
FIG. 35 is a graph showing release of sudan red dye from particles made using (■) 1:25 and (o) 2:25 VTMS:water (v/v), into ethanol, over time.

Two samples of sudan red dye (164 and 197 mg respectively) were stirred into NP-9 surfactant (1.25 g), followed by addition of distilled water (25 mL). Vinyltrimethoxysilane (1 and 2 mL respectively) was added with stirring, followed by addition of 3-aminopropyltriethoxysilane (1 and 2 mL respectively). The samples were stirred overnight, and the resulting solids separated by centrifugation (10,000 rpm, 10 minutes), and washed twice with distilled water. The encapsulation efficiencies were estimated to be 92 and 94% respectively, by analysis of the supernatant removed by centrifugation (approximately 14.3 and 9.1 wt % loading, respectively).
Release The samples (53.5 and 49.2 mg respectively) were suspended in ethanol (100 mL) with stirring. At each time point, 1.5 mL was extracted from both samples and centrifuged to isolate the solid, which was then returned to the solution with 1 mL of fresh ethanol. The extracted 1.5 mL was analysed by UV/Vis (absorbance at 536 nm), to determine the concentration of sudan red dye released into the supernatant. The release curve is shown in FIG. 35. The second sample released dye more quickly than the first, but by 100 minutes, both samples had released >90% of the encapsulated Sudan red dye.

Example 8

Encapsulation Efficiencies

Other experiments have been performed following the process of the invention to encapsulate the following hydrophobic active molecules in organosilica particles: Solvent Blue 35, Sudan red, Limonene and Retinol. The measured encapsulation efficiencies in the particles were as follows: Solvent Blue 35 (85%), Sudan red (52%), Limonene (23%) and Retinol (44%). The loading of the actives in the particles was about 10%. The diameters of the particles in each instance were in the range of 100 nm to 10 microns. The porosity of the particles when measured by BET was negligible but when measured by TEM showed that the particles were macroporous. In each instance the active was releasable from the particles into a solvent medium.

The invention claimed is:

1. A process for making particles, comprising:
   (A) forming an emulsion comprising a hydrophobic phase dispersed in a hydrophilic phase, wherein the hydrophobic phase comprises a dopant;
   (B) adding a precursor material to the emulsion wherein the precursor material migrates to the hydrophobic phase;
   (C) adding to the emulsion a catalyst composing an aminofunctional silane, wherein (i) the catalyst penetrates into the hydrophobic phase and (ii) the precursor material reacts in the presence of the catalyst to form particles comprising the dopant therein,
   wherein (i) each of the particles is a porous solid and (ii) the dopant is distributed substantially homogenously within and is releasable by diffusion from each particle.

2. The process of claim 1, wherein the dopant is a hydrophobic material.

3. The process of claim 1, wherein the emulsion is destabilized when the catalyst is added.

4. The process of claim 3, wherein the emulsion comprises droplets and the emulsion is destabilized as the size of the droplets increases.

5. The process claim 1, wherein the precursor comprises an organotrialkoxysilane.

6. The process of claim 5, wherein the organotrialkoxysilane is selected from the group consisting of ethyltrimethoxysilane, vinyltrimethoxysilane, phenyltrimethoxysilane, isopropyltrimethoxysilane, benzyltrimethoxysilane, ethyltriethoxysilane, vinyltriethoxysilane, phenyltriethoxysilane, isopropyltriethoxysilane and benzyltriethoxysilane.

7. The process of claim 1, wherein the dopant is selected from the group consisting of a fluorescent dye, a radiopharmaceutical, a drug, an enzyme, a catalyst, a hormone, a biocide, a flavour, an aroma substance, an oil, a nutraceutical, a vitamin supplement, and a mixture of any two or more thereof.

8. The process of claim 1, wherein the hydrophobic phase after adding the precursor material comprises between about 0.01% and about 50% of the dopant.

9. The process of claim 1, wherein the step of forming the emulsion comprises combining the hydrophobic phase, the hydrophilic phase and a surfactant to form a mixture and agitating the mixture.

10. The process of claim 9, wherein the surfactant is capable of dissolving the dopant.

11. The process of claim 1, wherein the catalyst is an aminoorganotrialkoxysilane.

12. The process of claim 1, wherein the aminofunctional silane is selected from a group consisting of 3-aminopropyltriethoxysilane (APTES), 3-(2-aminoethylamino)propyltrimethoxysilane (DATMS), 3-aminopropyltrimethoxysilane (APTMS) and 3-[2-(2-aminoethylamino)ethylamino]propyltrimethoxysilane (TATMS).

13. The process of claim 1, wherein the particles comprise the dopant in an organically modified ceramic matrix.

* * * * *